United States Patent [19]

Sugihara et al.

[11] Patent Number: 4,871,842

[45] Date of Patent: Oct. 3, 1989

[54] PIPERIDINE DERIVATIVES

[75] Inventors: Hirosada Sugihara, Osaka; Kohei Nishikawa, Kyoto; Katsumi Ito, Osaka, all of Japan

[73] Assignee: Takeda Chemical Industries, Ltd., Osaka, Japan

[21] Appl. No.: 218,951

[22] Filed: Jul. 14, 1988

Related U.S. Application Data

[63] Continuation of Ser. No. 806,810, Dec. 10, 1985, abandoned.

[30] Foreign Application Priority Data

| Dec. 21, 1984 | [WO] | PCT Int'l Appl. ... PCT/JP84/00608 |
| Feb. 8, 1985 | [WO] | PCT Int'l Appl. ... PCT/JP85/00052 |
| May 22, 1985 | [WO] | PCT Int'l Appl. ... PCT/JP85/00280 |
| Sep. 20, 1985 | [JP] | Japan ................... 60-209319 |

[51] Int. Cl.$^4$ .............................................. C07D 401/12
[52] U.S. Cl. ................... 540/523; 546/147; 546/201; 546/208; 546/195; 546/209; 546/121; 546/97; 546/232; 546/170; 546/15; 546/189; 546/200; 546/207; 546/210; 540/491; 540/521; 540/500
[58] Field of Search ............ 546/201, 208, 147; 540/523

[56] References Cited

FOREIGN PATENT DOCUMENTS

00/46953  3/1982  European Pat. Off. ............ 546/201
59-231052 12/1984  Japan .

*Primary Examiner*—Robert T. Bond
*Attorney, Agent, or Firm*—Wegner & Bretschneider

[57] ABSTRACT

Novel compounds of the formula:

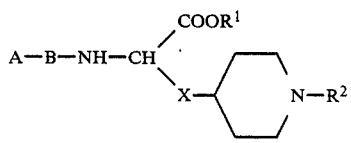

[wherein A is an α-amino acid residue; B is a group represented by the formula:

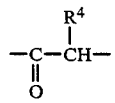

(wherein $R^4$ is hydrogen, lower alkyl, aralkyl or amino-lower alkyl), whereby the linkage between the symbols A and B designates a peptide bond and the group $R^4$ in B may be linked with A; $R^1$ is hydrogen, lower alkyl or aralkyl; $R^2$ is hydrogen, lower alkyl, aralkyl or acyl; X is alkylene] and salts thereof possess, for example, inhibitory activity on angiotensin converting enzyme, and are useful as an agent for diagnosis, prevention or treatment of hypertension as well as circulatory diseases such as cardiopathy and cerebral apoplexy.

10 Claims, No Drawings

PIPERIDINE DERIVATIVES

This application is a continuation of Ser. No. 806,810, filed Dec. 10, 1985, now abandoned.

TECHNICAL FIELD

This invention relates to novel piperidine derivatives which are of value as a pharmaceutical.

BACKGROUND ART

Although there have been known various compounds exhibiting inhibitory activity on angiotensin converting enzyme, any compound with such activity having a moiety of ω-(4-piperidyl)-α-amino acid has not been known at all.

The present inventors, after intensive search for the compound which exhibits inhibitory activity on angiotensin converting enzyme and is useful as a therapeutic agent for hypertension and circulatory diseases, such as cardiopathy and cerebral apoplexy, succeeded in producing the piperidine derivatives exhibiting excellent actions, and have completed this invention.

DISCLOSURE OF THE INVENTION

This invention provides compounds of the formula:

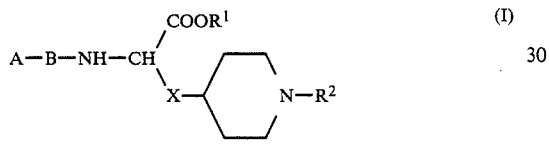

(I)

[wherein A is an α-amino acid residue; B is a group represented by the formula:

(wherein $R^4$ is hydrogen, lower alkyl, aralkyl or amino-lower alkyl), whereby the linkage between the symbols A and B designates a peptide bond and the group $R^4$ in B may be linked with A; $R^1$ is hydrogen, lower alkyl or aralkyl; $R^2$ is hydrogen, lower alkyl, aralkyl or acyl; X is alkylene] and salts thereof.

In the above formulae, the α-amino acid residue as represented by A includes, for example, chain α-amino acid residues, such as alanino, $N^\alpha$-arginino, $N^\alpha$-asparagino, glycino, $N^\alpha$-histidino, leucino, $N^\alpha$-lysino, cysteino, tryptophano, thyrosino and valino; α-amino acid residues which constitute such chain α-amino acid residues having their carboxyl groups esterified; and groups represented by the formulae:

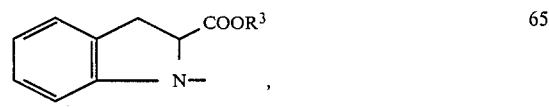

-continued

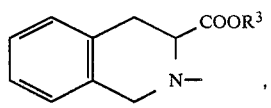

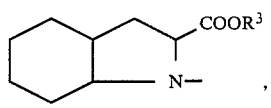

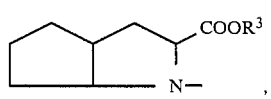

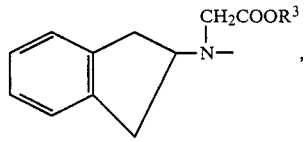

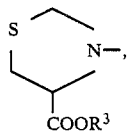

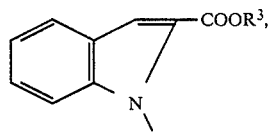

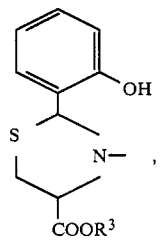

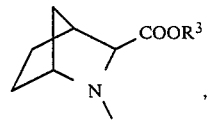

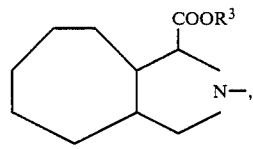

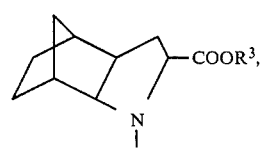

-continued
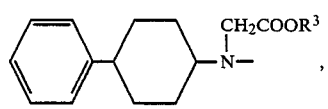
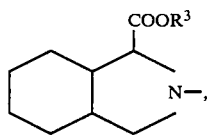
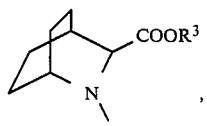
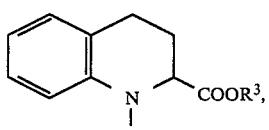
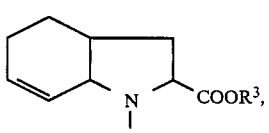
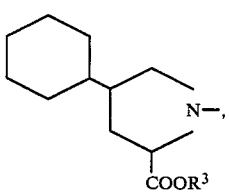
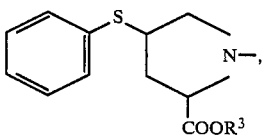
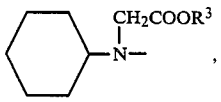
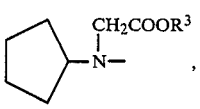
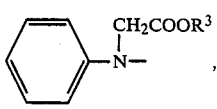
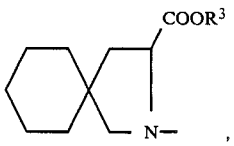
-continued
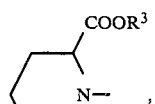
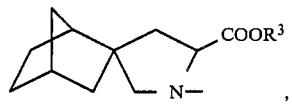
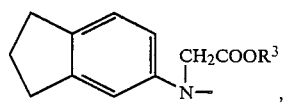
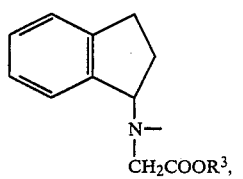
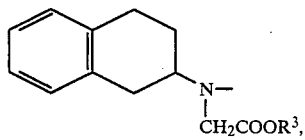
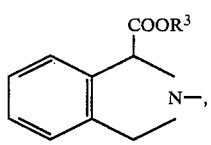
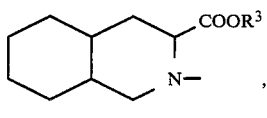
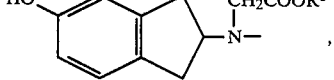
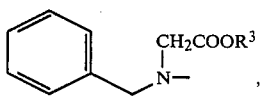
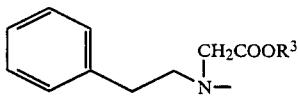
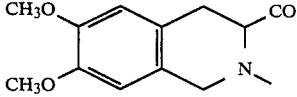
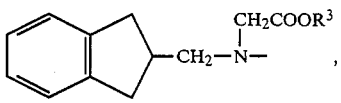

-continued
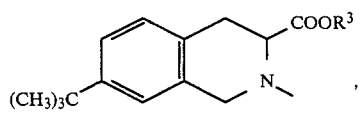
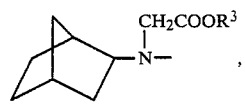
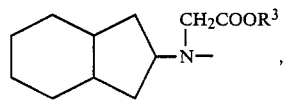
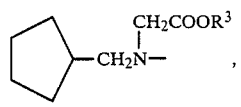
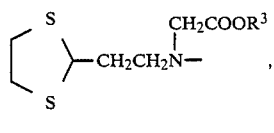
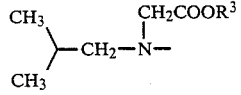
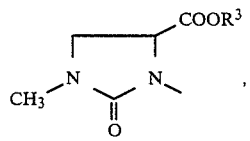
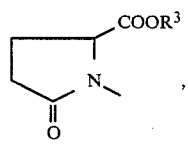
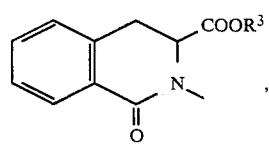
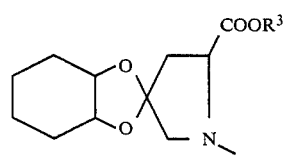
and
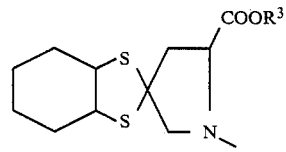
wherein $R^3$ is hydrogen, lower alkyl or aralkyl.
The group which the group $R^4$ in B combines with A to form includes, for example, groups as represented by the formulae:
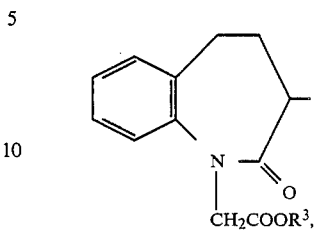
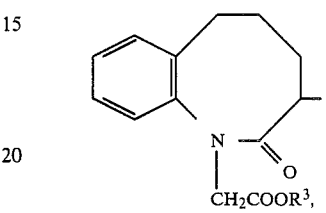
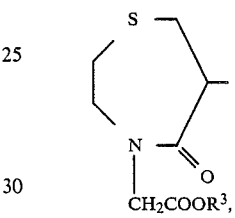
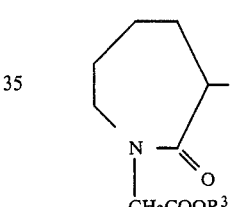
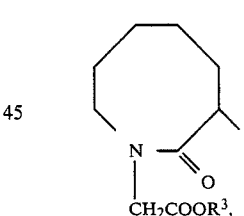
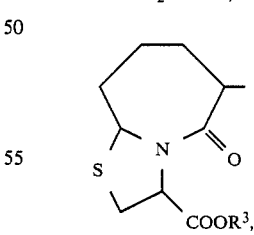
and
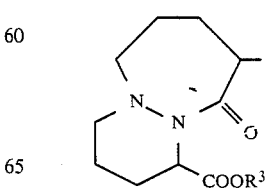

-continued

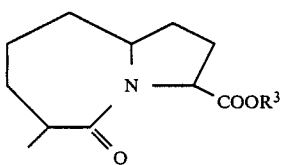

[wherein R³ is hydrogen, lower alkyl or aralkyl].

The esterified carboxyl group contained in the above chain α-amino acid residues includes, for example, lower-($C_{1-4}$)-alkoxycarbonyl and aralkyloxycarbonyl, such as phenyl-lower-($C_{1-4}$)-alkoxycarbonyl.

With reference to the above formula (I), the lower alkyl group represented by $R^1$, $R^2$, $R^3$ or $R^4$ includes alkyl groups of about 1 to 4 carbon atoms, such as methyl, ethyl, propyl, isopropyl, butyl, isobutyl, sec-butyl and tert-butyl. The aralkyl group represented by $R^1$, $R^2$, $R^3$ or $R^4$ includes phenyl-lower($C_{1-4}$)-alkyl groups, such as benzyl, phenethyl, 3-phenylpropyl, α-methylbenzyl, α-ethylbenzyl, α-methylphenethyl, β-methylphenethyl and β-ethylphenethyl.

The acyl group represented by $R^2$ includes lower-($C_{1-5}$)-alkanoyl (e.g., acetyl, propionyl), benzoyl, phenyl-lower($C_{1-4}$)-alkoxycarbonyl (e.g., benzyloxycarbonyl) and lower-($C_{1-4}$)-alkoxycarbonyl (e.g., tert-butoxycarbonyl) groups.

The amino-lower alkyl group represented by $R^4$ inlcudes amino-lower alkyl groups of about 1 to 4 carbon atoms, such as aminoethyl, aminopropyl and aminobutyl.

The alkylene chain represented by X includes, for example, straight-chain or branched-chain alkylene chains of about 1 to 7 carbon atoms, being exemplified by divalent groups, such as methylene, ethylene, trimethylene, tetramethylene, pentamethylene, hexamethylene, heptamethylene, propylene, ethylmethylene and dimethyltetramethylene. The said alkylene bridges may have in the chain an unsaturated bond or unsaturated bonds (e.g., double bond, triple bond).

Specific disclosure of compounds of this invention includes, for example, the compounds as shown in Tables 1 to 5.

TABLE 1

$$A-B-NH-CH\begin{matrix}COOR^1\\X-\bigcirc N-R^2\end{matrix}$$

| A | B | X | $R^1$ | $R^2$ |
|---|---|---|---|---|
| COOH ⟨N—⟩ | —C(=O)—CH(CH₃)— | —(CH₂)₄— | H | H |
| COOH ⟨N—⟩ | —C(=O)—CH(CH₃)— | —(CH₂)₄— | $C_2H_5$ | H |
| COOH ⟨N—⟩ | —C(=O)—CH(CH₃)— | —(CH₂)₄— | $C_2H_5$ | COOCH₂Ph |
| COOH ⟨N—⟩ | —C(=O)—CH((CH₂)₄NH₂)— | —(CH₂)₄— | H | H |
| COOH ⟨N—⟩ | —C(=O)—CH((CH₂)₄NH₂)— | —(CH₂)₄— | $C_2H_5$ | H |
| COOH ⟨N—⟩ | —C(=O)—CH((CH₂)₄NH₂)— | —(CH₂)₄— | $C_2H_5$ | COOCH₂Ph |

TABLE 1-continued $$A-B-NH-CH\begin{matrix}COOR^1\\X\end{matrix}\text{-piperidine-}N-R^2$$

| A | B | X | R¹ | R² |
|---|---|---|----|----|
| 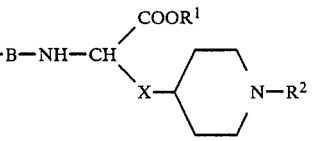 (2-indanyl-N-CH₂COOH) | −C(O)−CH(CH₃)− | −(CH₂)₄− | H | H |
|  (2-indanyl-N-CH₂COOH) | −C(O)−CH(CH₃)− | −(CH₂)₄− | C₂H₅ | H |
|  (2-indanyl-N-CH₂COOH) | −C(O)−CH(CH₃)− | −(CH₂)₄− | C₂H₅ | COOCH₂Ph |
| 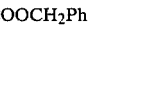 (tetrahydroisoquinoline-COOH) | −C(O)−CH(CH₃)− | −(CH₂)₄− | H | H |
|  (tetrahydroisoquinoline-COOH) | −C(O)−CH(CH₃)− | −(CH₂)₄− | C₂H₅ | H |
|  (tetrahydroisoquinoline-COOH) | −C(O)−CH(CH₃)− | −(CH₂)₄− | C₂H₅ | COOCH₂Ph |
| 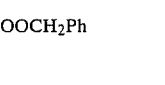 (octahydrocyclopenta[b]pyrrole-2-COOH) | −C(O)−CH(CH₃)− | −(CH₂)₄− | H | H |
|  (octahydrocyclopenta[b]pyrrole-2-COOH) | −C(O)−CH(CH₃)− | −(CH₂)₄− | C₂H₅ | H |
|  (octahydroindole-2-COOH) | −C(O)−CH(CH₃)− | −(CH₂)₄− | H | H |
|  (octahydroindole-2-COOH) | −C(O)−CH(CH₃)− | −(CH₂)₄− | C₂H₅ | H |
|  (indoline-2-COOH) | −C(O)−CH(CH₃)− | −(CH₂)₄− | H | H |

TABLE 1-continued
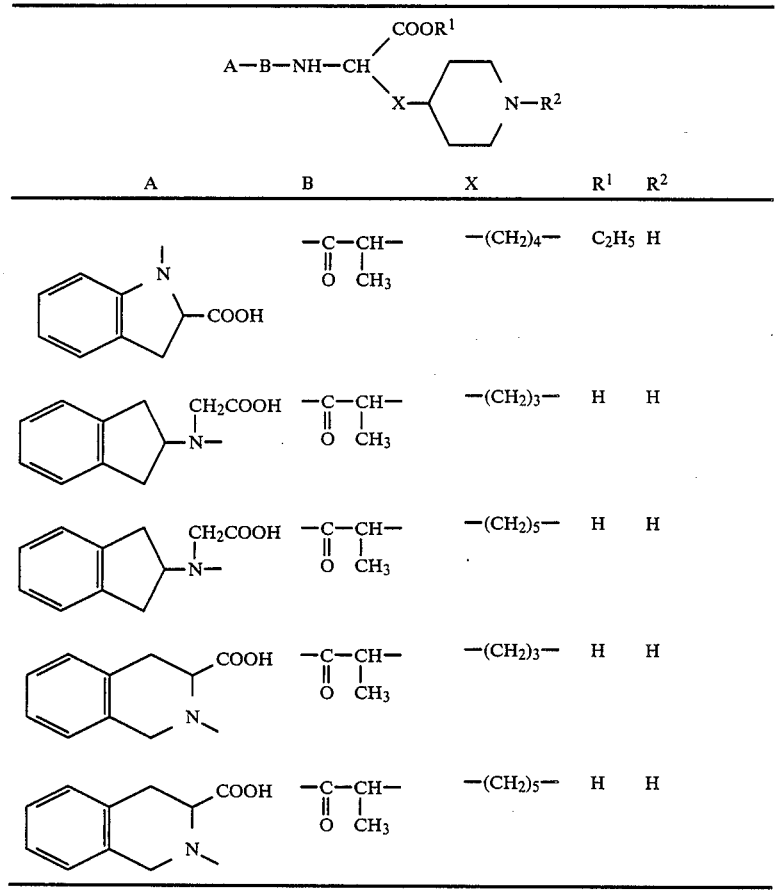
TABLE 2
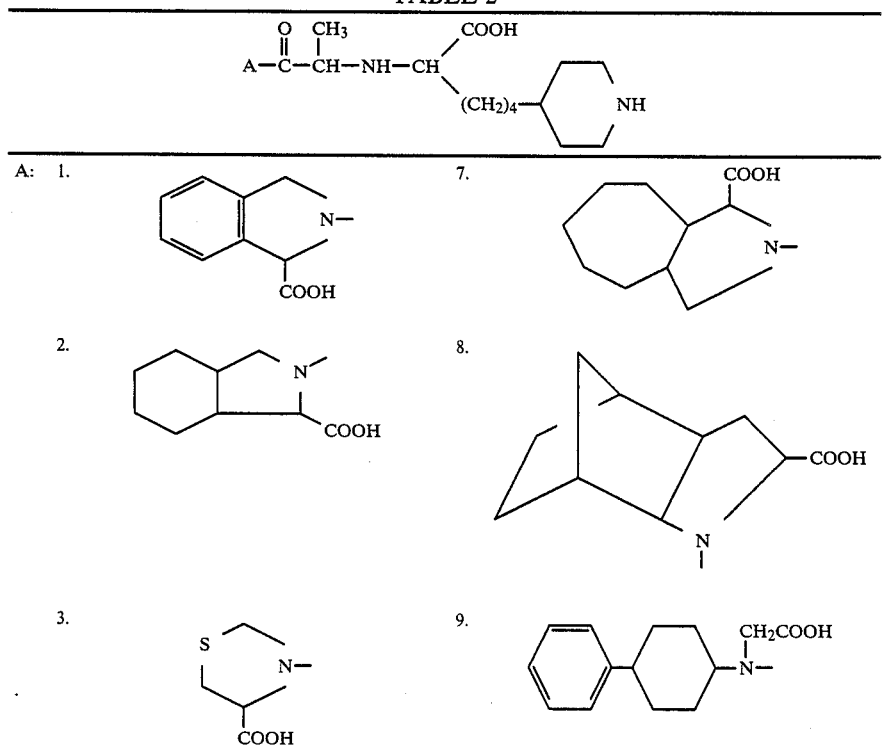

TABLE 2-continued
$$A-\overset{O}{\underset{\|}{C}}-\overset{CH_3}{\underset{|}{C}H}-NH-\overset{COOH}{\underset{|}{C}H}-(CH_2)_4-\underset{}{\bigcirc}NH$$
4. 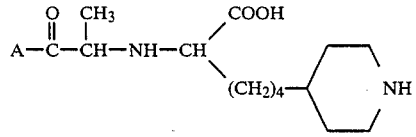
5. 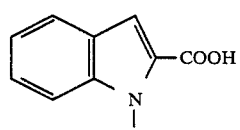
6. 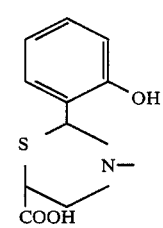
10. 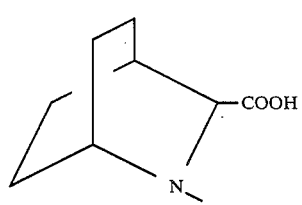
11. 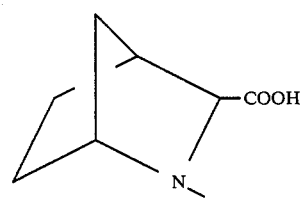
12. 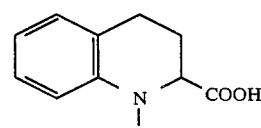
13. 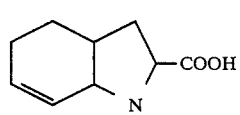
14. 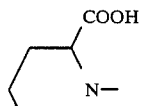
15. 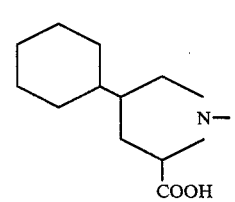
16. 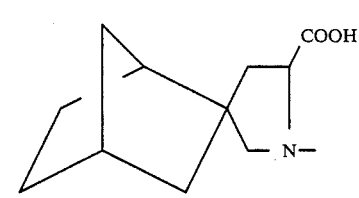
19. 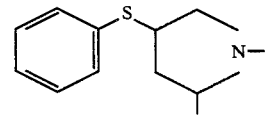
20. 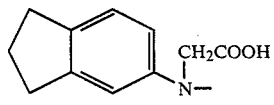
21. 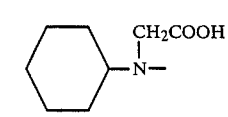
22. 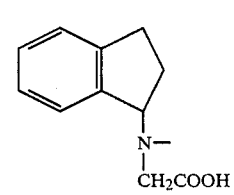
23. 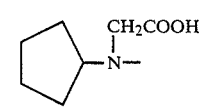

TABLE 2-continued

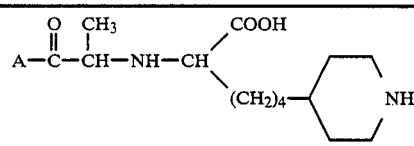

| 17. | (phenyl)N−CH2COOH |
| 18. | (spiro cyclohexane-cyclopentane with CH3, CH2COOH, N−) |
| 24. | (decahydroisoquinoline with COOH, N−) |
| 25. | HO-(indane)-N(CH2COOH)− |
| 26. | (phenyl)CH2-N(CH3)-CH2COOH |
| 27. | (phenyl)CH2CH2-N−CH2COOH |
| 28. | CH3O, CH3O-(tetrahydroisoquinoline)-COOH, N− |
| 29. | (indanyl)-CH2-N−CH2COOH |
| 30. | (CH3)3C-(tetrahydroisoquinoline)-COOH, N− |
| 31. | (norbornyl)-N−CH2COOH |
| 33. | (cyclopentyl)-CH2N−CH2COOH |
| 34. | (dithiolane)CH-CH2CH2N−CH2COOH |
| 35. | (CH3)2CH-CH2N−CH2COOH |
| 36. | CH3-N, N-CH3 urea with CH2, COOH |
| 37. | (N-methylpyrrolidinone)-COOH |
| 38. | (dihydroisoquinolinone)-COOH, N− |
| 39. | (cyclohexane-dioxolane spiro pyrrolidine)-COOH, N− |
| 40. | (cyclohexane-dithiolane spiro pyrrolidine)-COOH, N− |

TABLE 2-continued

A—C(=O)—CH(CH₃)—NH—CH(COOH)—(CH₂)₄—[4-piperidinyl-NH]

32. [decahydroindan-2-yl]—N(CH₂COOH)—

TABLE 3

A—B—NH—CH(COOR¹)—X—[4-(1-R²-piperidinyl)]

| A—B— | X | R¹ | R² |
|---|---|---|---|
| [2,3,4,5-tetrahydro-1H-1-benzazepin-2-one, 3-yl with N-CH₂COOH] | —(CH₂)₄— | H | H |
| [same benzazepinone] | —(CH₂)₄— | C₂H₅ | H |
| [same benzazepinone] | —(CH₂)₄— | C₂H₅ | COOCH₂Ph |
| [same benzazepinone] | —(CH₂)₃— | H | H |
| [same benzazepinone] | —(CH₂)₅— | H | H |

TABLE 4

A—B—NH—CH(COOH)—(CH₂)₄—[4-piperidinyl-NH]

A—B—:

1. [2,3,4,5-tetrahydro-1H-1-benzazepin-2-one, 3-yl with N-CH₂COOH]

6. [hexahydropyridazino-azepinone with COOH]

TABLE 4-continued
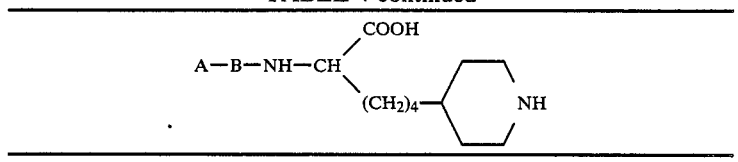
2. 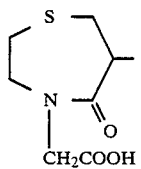   7. 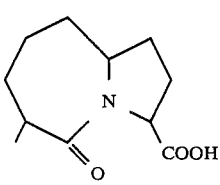
3. 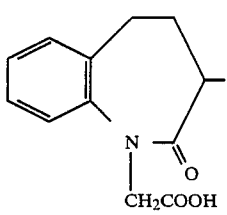
4. 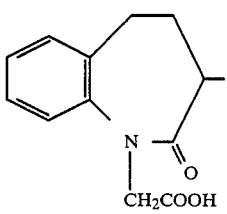
5. 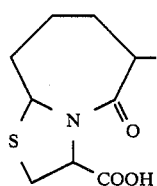
TABLE 5
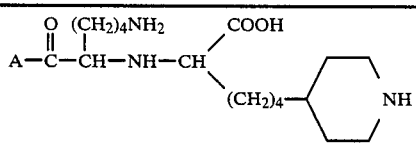
A:1. 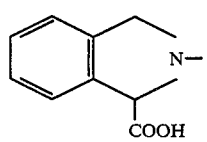   7. 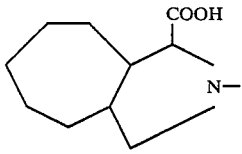
2. 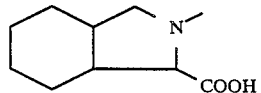   8. 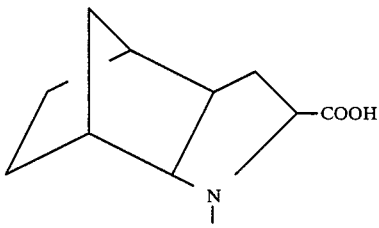

TABLE 5-continued
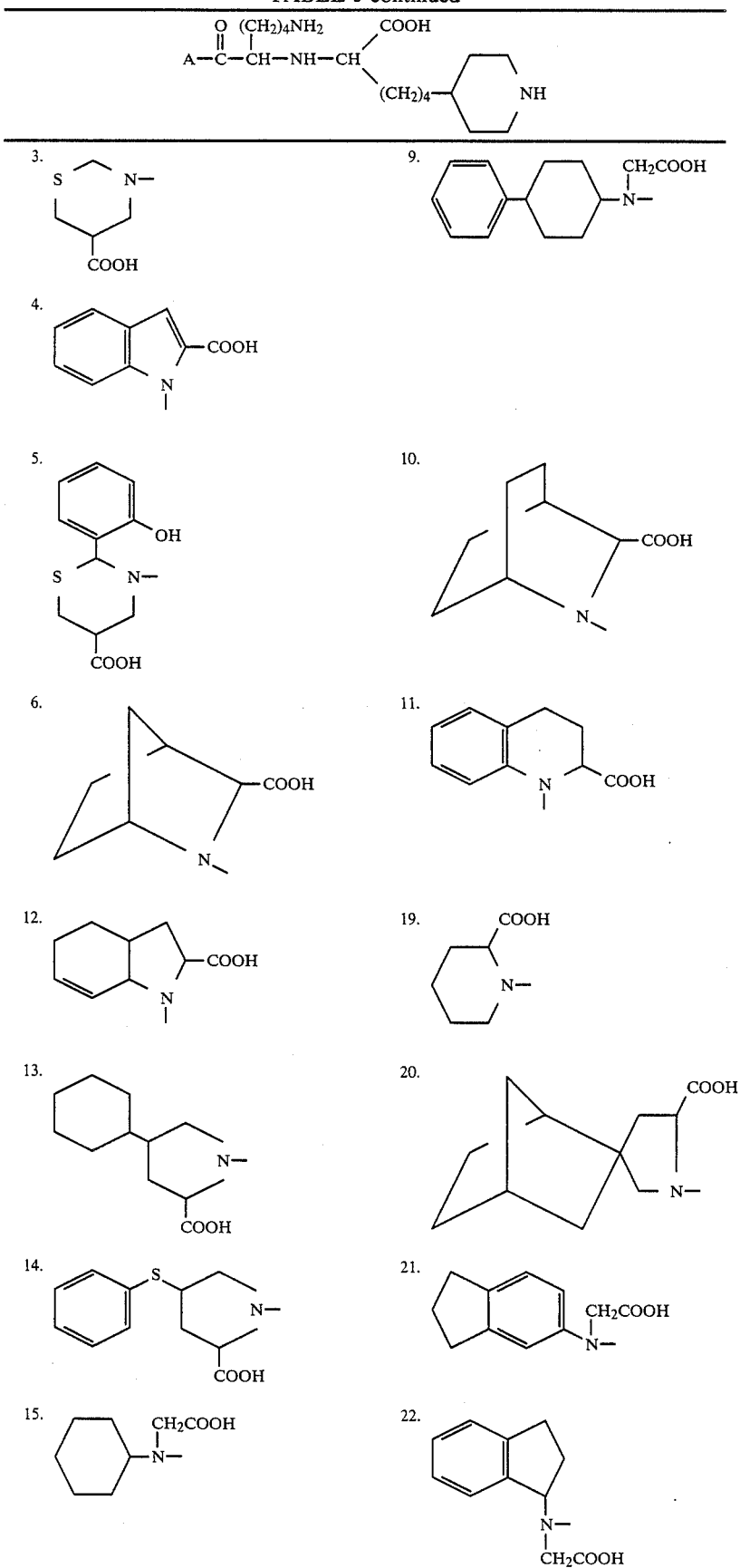

TABLE 5-continued
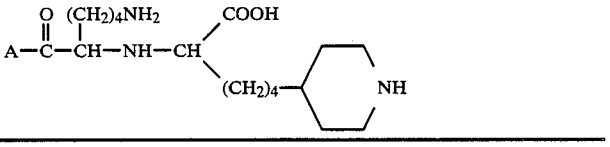
16. 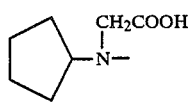
17. 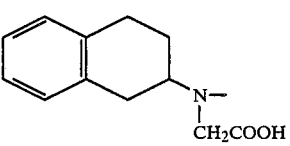
18. 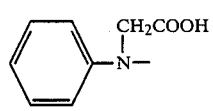
24. 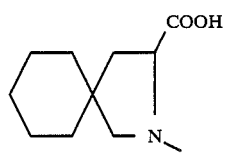
25. 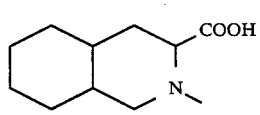
26. 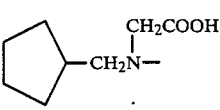
27. 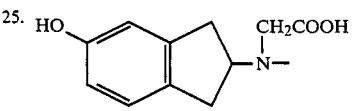
28. 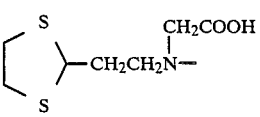
29. 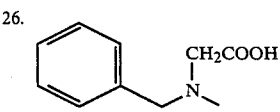
30. 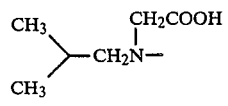
23. 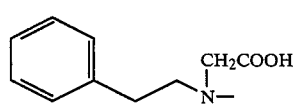
33. 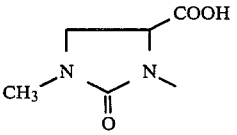
34. 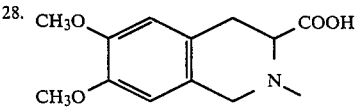
35. 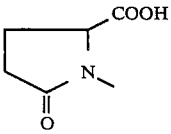
36. 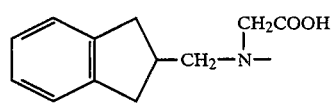
37. 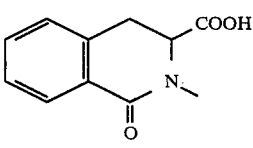
38. 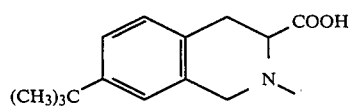
39. 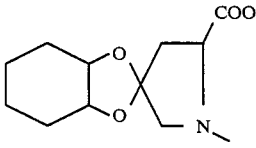

TABLE 5-continued

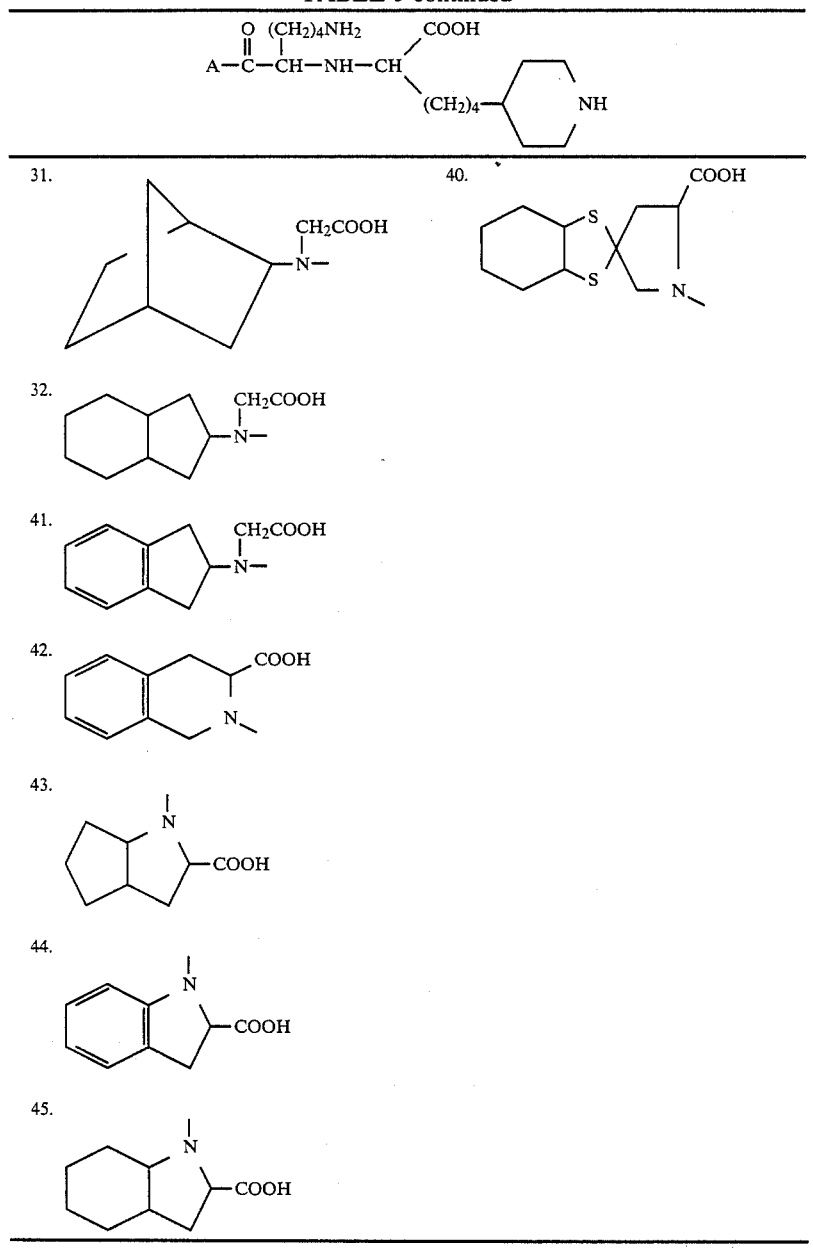

[wherein Ph is phenyl]

$R^1$ is preferably hydrogen or lower alkyl; $R^2$ is desirably hydrogen; $R^3$ is favorably hydrogen; and $R^4$ is preferably lower alkyl or amino-lower-alkyl or linked with A, more preferably lower alkyl. X is preferably trimethylene, tetramethylene or pentamethylene; X is more preferably tetramethylene.

A—B— is preferably a group represented by the formula:

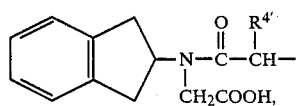

(i)

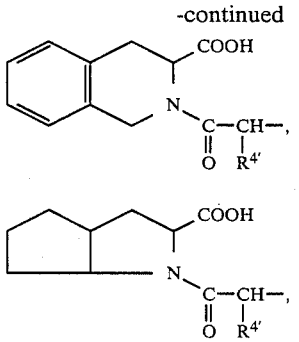

-continued

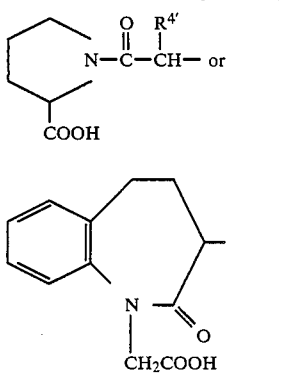

[wherein $R^{4'}$ is lower-$(C_{1-4})$-alkyl], more preferably a group represented by the formula (i) or (ii).

The compound (I) of this invention contains an asymmetric carbon atom in the molecule, and its isomers with the R- and S-configurations and a mixture thereof all fall within the scope of this invention.

The salt of the compound (I) includes pharmaceutically acceptable salts, such as inorganic acid salts being exemplified by hydrochloride, hydrobromide, sulfate, nitrate and phosphate; organic acid salts being exemplified by acetate, tartarate, citrate, fumarate, maleate, toluenesulfonate and methanesulfonate; metal salts exemplified by sodium salt, potassium salt, calcium salt and aluminum salt; and salts with bases being exemplified by triethylamine salt, guanidine salt, ammonium salt, hydrazine salt, quinine salt and cinchonine salt.

The compound (I) of this invention can be produced, for example, by subjecting a compound of the formula:

   (II)

[wherein the symbol is as defined hereinbefore] and a compound of the formula:

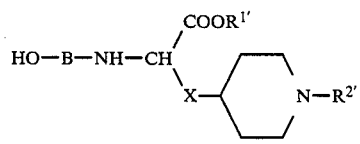

wherein $R^{1'}$ is a lower alkyl or aralkyl group corresponding to $R^1$; $R^{2'}$ is an acyl group corresponding to $R^2$; other symbols are as defined hereinbefore] to a dehydration condensation reaction.

The said dehydration condensation reaction can be carried out, for example, by means of an ordinary amide bond formation reaction in peptides. Thus, the reaction can be conducted by employing a peptide forming reagent solely, such as dicyclohexylcarbodiimide, N,N'-carbonyldiimidazole, diphenylphosphorylazide or diethyl phosphorocyanidate or subjecting the compound (III) to condensation with a phenol compound such as 2,4,5-trichlorophenol, pentachlorophenol, pentafluorophenol, 2-nitrophenol or 4-nitrophenol, or an N-hydroxy compound, such as N-hydroxysuccinimide, 1-hydroxybenzotriazole or N-hydroxypiperidine, in the presence of a catalyst, such as dicyclohexylcarbodiimide to convert the compound (III) into an active ester derivative, followed by dehydration condensation with the compound (II). The said dehydration reaction, whether it comprises subjecting to the reaction the compound (III) as such or after converting into an active ester derivative, can be accelerated by adding preferably an organic base, such as a quarternary ammonium salt or a tertiary amine (e.g., triethylamine, N-methylpiperidine). The reaction temperature is normally $-20°$ to $+50°$ C., preferably in the neighborhood of room temperature, and the solvent to be ordinarily employed includes, for example, dioxane, tetrahydrofuran, acetonitrile, pyridine, N,N-dimethylformamide, N,N-dimethylacetamide, dimethylsulfoxide, N-methylpyrrolidone, chloroform and methylene chloride, whereby these may be used singly or as a mixture thereof.

The compound (I) of this invention can also be produced, for example, by reacting a compound of the formula:

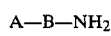   (IV)

[wherein each of the symbols is as defined hereinbefore] with a compound of the formula:

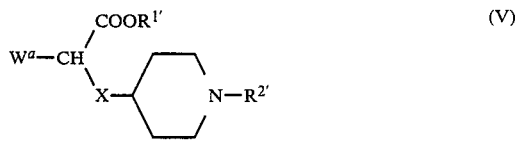

[wherein $R^{1'}$, $R^{2'}$ and X are defined hereinbefore; $W^a$ is halogen or a group represented by the formula $R^a$—SO$_2$—O— (wherein $R^a$ is lower-$(C_{1-4})$-alkyl, trifluoromethyl, phenyl or p-tolyl); other symbols are as defined hereinbefore]. The reaction can normally be allowed to proceed by maintaining the compounds in the presence or absence of water of an organic solvent (e.g., acetonitrile, dimethylformamide, dimethylsulfoxide, tetrahydrofuran, benzene, toluene), solely or as a mixture thereof, in the temperature range of about $-20°$ to $+150°$ C., whereby for the purpose of accelerating the reaction rate, a base, such as potassium carbonate, sodium hydroxide, sodium hydrogencarbonate, pyridine or triethylamine, can also be allowed to coexist in the reaction system.

Alternatively, the compound (I) of this invention can be produced, for example, by subjecting the compound of the formula (IV) and a compound of the formula:

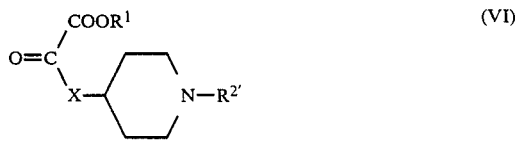

[wherein each of the symbols is as defined hereinbefore] to a condensation reaction under reductive conditions.

The said reductive conditions include, for example, reaction conditions, such as catalytic reduction using a metal, such as platinum, palladium, rhodium or Raney nickel, or a mixture thereof with an arbitrary carrier (e.g., carbon, barium sulfate, calcium sulfate, barium carbonate, calcium carbonate) as a catalyst; reduction with a metal hydride compound, such as lithium aluminum hydride, lithium borohydride, lithium cyanoborohydride, sodium borohydride or sodium cyanoborohydride; reduction with metallic sodium, metallic magnesium, or the like and an alcohol; reduction with a metal, such as iron or zinc, and an acid, such as hydrochloric acid or acetic acid; electrolytic reduction; and reduction with a reducing enzyme. The above reaction is normally carried out in the presence of water or an organic solvent (e.g., methanol, ethanol, ethyl ether, dioxane, methylene chloride, chloroform, benzene, toluene, acetic acid, dimethylformamide, dimethylacetamide, and the reaction temperature varies with means of reduction employed, but generally is preferably in the range of −20° to +100° C. This reaction can be conducted at atmospheric pressure to achieve the desired object satisfactorily but may also be carried out under pressure or under reduced pressure according to the circumstances.

Also, the compound (I) of this invention can be produced, for example, by subjecting a compound of the formula:

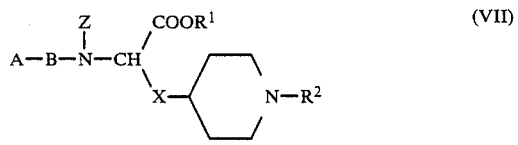

(VII)

[wherein Z is a protecting group removable by hydrolysis or catalytic reduction; and other symbols are as defined hereinbefore] to a hydrolysis or catalytic reduction reaction. As the protecting group removable by hydrolysis as represented by Z in the formula (VII), there are used all kinds of acyl and trityl groups, and among others, benzyloxycarbonyl, tert-butoxycarbonyl, trifluoroacetyl, trityl, etc. are advantageous in the case of a reaction under relatively mild reaction conditions. The protecting group removable by catalytic reduction as represented by Z includes, for example, benzyl, diphenylmethyl and benzyloxycarbonyl. The hydrolysis reaction in this procedure is carried out in water or an organic solvent, such as methanol, ethanol, dioxane, pyridine, acetic acid, acetone or methylene chloride or a mixture thereof, and can also be conducted, for the purpose of accelerating the reaction rate, by adding an acid (e.g., hydrogen chloride, hydrogen bromide, hydrogen iodide, hydrogen fluoride, sulfuric acid, methanesulfonic acid, p-toluenesulfonic acid, trifluoroacetic acid) or a base (e.g., sodium hydroxide, potassium hydroxide, potassium carbonate, sodium hydrogencarbonate, sodium acetate, triethylamine). The above reaction is normally carried out in the temperature range of about −20° to +150° C. The catalytic reduction reaction in this procedure is conducted in water or an organic solvent, such as methanol, ethanol, dioxane or tetrahydrofurane, or a mixture thereof in the presence of a suitable catalyst, such as platinum or palladium-carbon. This reaction is carried at atmospheric pressure or under pressure up to about 150 kg/cm² and at ambient temperature or at a temperature up to +150° C., although it generally proceeds satisfactorily at ambient temperature and at atmospheric pressure.

Furthermore, the compound (I) of this invention can be produced by solvolysis of the cyano group of a compound of the formula:

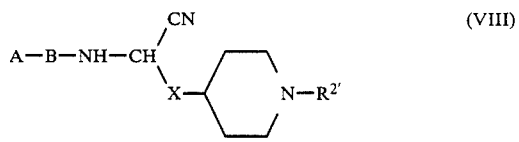

(VIII)

[wherein each of the symbols is as defined hereinbefore].

The above solvolysis reaction is carried out in water or an organic solvent, such as methanol, ethanol, dioxane, pyridine, acetic acid, acetone or methylene chloride, or a mixture thereof, and can also be carried out, for the purpose of accelerating the reaction rate, by adding an acid (e.g., hydrogen chloride, hydrogen bromide, hydrogen iodide, hydrogen fluoride, sulfuric acid, methanesulfonic acid, p-toluenesulfonic acid, trifluoroacetic acid, acidic resin) or a base (e.g., sodium hydroxide, potassium hydroxide, potassium carbonate, sodium hydrogencarbonate, sodium acetate, triethylamine). The reaction is normally carried out in the temperature range of about −20° to +150° C.

The compound of the formula (I) wherein $R^1$ is hydrogen or/and $R^3$ is hydrogen can be produced by subjecting the compound of the formula (I) wherein $R^1$ is lower alkyl or/and $R^3$ is lower alkyl to a hydrolysis or elimination reaction, and also by subjecting the compound of the formula (I) wherein $R^1$ is benzyl or/and $R^3$ is benzyl to a catalytic reduction reaction. The hydrolysis or elimination reaction in this procedure is carried out in water or an organic solvent, such as methanol, ethanol, ethyl acetate, chlorform, tetrahydrofuran, dioxane, pyridine, acetic acid, acetone or methylene chloride, or a mixture thereof, and can also be conducted by adding an acid (e.g., hydrogen chloride, hydrogen bromide, hydrogen fluoride, hydrogen iodide, sulfuric acid, methanesulfonic acid, p-toluenesulfonic acid, trifluoroacetic acid) or a base (e.g., sodium hydroxide, potassium hydroxide, potassium carbonate, sodium hydrogencarbonate, sodium carbonate, sodium acetate). The above reaction is normally carried out in the temperature range of about −20° to +150° C. Also, the catalytic reduction reaction in this procedure is conducted in water or an organic solvent, such as methanol, ethanol, ethyl acetate, dioxane or tetrahydrofuran, or a mixture thereof, in the presence of a suitable catalyst, such as palladium-carbon. This reaction is carried out at atmospheric pressure or under pressure up to about 150 kg/cm² and at ambient temperature or at a temperature up to +150° C.

The compound of the formula (I) wherein $R^1$ is lower alkyl or aralkyl or/and $R^3$ is lower alkyl or aralkyl can be produced by subjecting the compound of the formula (I) wherein $R^1$ is hydrogen or/and $R^3$ is hydrogen and a compound of the formula:

(IX)

or a compound of the formula:

(X)

[wherein $R^{1'}$ and $R^{3'}$ are lower alkyl or aralkyl] to a condensation reaction.

The conditions of the said condensation reaction include, for example, reaction conditions, such as condensation using a condensing agent (e.g., dicyclohexylcarbodiimide, carbonyldiimidazole, diethyl phosphorocyanidate, diphenyl phosphorylazide) or condensation employing an acid catalyst (e.g., hydrogen chloride, hydrogen bromide, p-toluenesulfonic acid). The reaction proceeds in the presence or absence of a suitable solvent (e.g., dimethylformamide, acetonitrile, tetrahydrofuran, methylene chloride) or a mixture thereof, in the temperature range of about −20° to +150° C.

The compound of the formula (I) wherein $R^1$ is lower alkyl or aralkyl or/and $R^3$ is lower alkyl or aralkyl can also be produced by reacting the compound of the formula (I) wherein $R^1$ is hydrogen or/and $R^3$ is hydrogen with a compound of the formula:

$$R^{1''}-W^b \quad (XI)$$

or a compound of the formula:

$$R^{3''}-W^b \quad (XII)$$

[wherein $R^{1''}$ and $R^{3''}$ are lower alkyl or aralkyl; $W^b$ is halogen or a group represented by the formula $R^bSO_2-O-$ (wherein $R^b$ is lower-$(C_{1-4})$-alkyl, trifluoromethyl, phenyl or p-tolyl)]. The reaction proceeds in a suitable solvent (e.g., dimethylformamide, acetonitrile, dimethylsulfoxide, tetrahydrofuran) in the temperature range of about −20° to +150° C. in the presence of a base (e.g., potassium hydroxide, sodium hydroxide, sodium hydrogencarbonate, potassium hydrogencarbonate).

The compound (I) of this invention wherein the group $R^2$ is hydrogen can be produced by subjecting the compound of the formula (I) wherein the group $R^2$ is benzyl or acyl to a catalytic reduction, elimination or solvolysis reaction.

The catalytic reduction reaction in this procedure is carried out in water or an organic solvent, such as methanol, ethyl acetate, ethanol, dioxane or tetrahydrofuran, or a mixture thereof in the presence of a suitable catalyst, such as palladium-carbon. This reaction is conducted at atmospheric pressure or under pressure up to about 150 kg/cm² and at ambient temperature or at a temperature up to +150° C.

Also, the solvolysis or elimination reaction in this procedure is carried out in water or an organic solvent, such as methanol, ethanol, ethyl acetate, chloroform, tetrahydrofuran, dioxane, pyridine, acetic acid, acetone and methylene chloride, or a mixture thereof, and can also be conducted by adding an acid (e.g., hydrogen chloride, hydrogen bromide, hydrogen fluoride, hydrogen iodide, sulfuric acid, methanesulfonic acid, p-toluenesulfonic acid, trifluoroacetic acid) or a base (e.g., sodium hydroxide, potassium hydroxide, potassium carbonate, sodium hydrogencarbonate, sodium carbonate, sodium acetate). The above reaction is normally carried out in the temperature range of about −20° to +150° C.

The compound of the formula (I) wherein the group $R^2$ is lower alkyl, aralkyl or acyl can be obtained by reacting the compound of the formula (I) wherein $R^2$ is hydrogen with a compound of the formula:

$$R^{2''}-W^c \quad (XIII)$$

[wherein $R^{2''}$ is lower alkyl, aralkyl or acyl; $W^c$ is halogen or a group represented by the formula $R^cSO_2-O-$ (wherein $R^c$ is lower-$(C_{1-4})$-alkyl, trifluoromethyl, phenyl or p-tolyl)]. The reaction proceeds by maintaining both of the compounds in a suitable solvent (e.g., dimethylformamide, acetonitrile, dimethylsulfoxide, tetrahydrofuran) in the temperature range of about −20° to +150° C. In this case, a base such as potassium carbonate, sodium hydroxide, sodium hydrogencarbonate, pyridine or triethylamine can be allowed to coexist in the reaction system as a deacidifying agent for the purpose of accelerating the reaction rate.

Also, the compound of the formula (I) wherein the group $R^2$ is lower alkyl or aralkyl can be obtained by subjecting the compound of the formula (I) wherein the group $R^2$ is hydrogen and a lower-$(C_{1-4})$-alkylaldehyde or aralkylaldehyde [e.g., phenyl-lower-$(C_{1-4})$-alkylaldehydes] to condensation under reductive conditions.

The said reductive conditions include, for example, reaction conditions, such as catalytic reduction using a metal, such as platinum, palladium, rhodium or Raney nickel, or a mixture thereof with an arbitrary carrier (e.g. carbon, barium sulfate, calcium sulfate, barium carbonate calcium carbonate) as a catalyst; reduction with a metal hydride compound, such as lithium aluminum hydride, lithium borohydride, lithium cyanoborohydride, sodium borohydride or sodium cyanoborohydride; reduction with metallic sodium, metallic magnesium, or the like and an alcohol; reduction with a metal, such as iron or zinc, and an acid, such as hydrochloric acid or acetic acid; electrolytic reduction and reduction with a reducing enzyme. The above reaction is normally carried out in water or an organic solvent (e.g., methanol, ethanol, ethyl ether, dioxane, methylene chloride, chloroform, benzene, toluene, acetic acid, dimethylformamide, dimethylacetamide), and the reaction temperature varies with the means of reduction employed, but generally is preferably in the range of −20° C. to +100° C. This reaction can be conducted at atmospheric pressure to achieve the object satisfactorily, but may be carried out under pressure or under reduced pressure according to the circumstances.

The compound of the formula (I) wherein the group $R^2$ is acyl can also be produced by reacting the compound of the formula (I) wherein the group $R^2$ is hydrogen with a compound of the formula:

$$(R^{2'''})_2O \quad (XIV)$$

[wherein $R^{2'''}$ is acyl corresponding to $R^2$].

The reaction is allowed to proceed by maintaining both of the compounds in water or an organic solvent (e.g., ethyl acetate, ethyl ether, tetrahydrofuran, methylene chloride, chloroform, benzene) or a mixture thereof in the temperature range of about −20° to +150° C. In this case, a base such as potassium carbonate, sodium hydroxide, sodium hydrogencarbonate, pyridine or triethylamine can also be allowed to coexist in the reaction system as a deacidifying agent for the purpose of accelerating the reaction rate.

The salt of the compound (I) can be obtained by the production reaction for the compound (I) itself, but can also be produced by adding an acid, alkali or base, if desired.

The objective compound (I) of this invention thus obtained can be isolated from the reaction mixture by employing conventional separation and purification means, such as extraction, concentration, neutralization, filtration, recrystallization, column chromatography and thin-layer chromatography.

With reference to the compound (I), at least two stereoisomers can exist. These individual stereoisomers and mixtures thereof all fall within the scope of this invention, and these isomers can be produced individually, if desired. By carrying out the above reaction using a single isomer each of the starting compounds (II), (III), (IV), (V), (VII) and (VIII), for example, there can be obtained the single optical isomer of the compound (I), and in cases in which the resulting product consists of a mixture of at least two kinds of the isomers, it can be separated into the individual isomers by means of conventional separation procedures, such as the procedure of forming salts with an optically active acid (e.g., camphorsulfonic acid, tartaric acid, benzoyltartaric acid, etc.) or an optically active base (e.g., cinchonine, cinchonidine, quinine, quinidine, α-methylbenzylamine, dehydroabietylamine, etc.) and separation means being exemplified by a variety of chromatography and fractionation recrystallization.

The compound of this invention, namely the compound represented by the formula (I) and a salt thereof, exhibit inhibitory activities on angiotensin converting enzyme, bradikinin decomposing enzyme (kininase), etc. in animals, in particular, mammals (e.g., human, dog, cat, rabbit, guinea pig, rat), and are useful, for example, as a drug for diagnosis, prevention or treatment for hypertension, hypertensioninduced circulatory diseases, such as cardiopathy and cerebral apoplexy. The compound of this invention is low in toxicity, well absorbed even on oral administration and excellent in long-lasting effect and stability. Therefore, when the compound is used as the above-mentioned drug, it can be safely administered orally or parenterally, per se or in admixture with a suitable, pharmaceutically acceptable carrier, excipient or diluent into a pharmaceutical formulation, such as powder, granule, tablet, capsule or injectable solution. The dosage level varies depending upon the conditions of the disease to be treated and administration route employed, but in the case of administration to an adult patient for the purpose of treatment of renal or essential hypertension, for example, the compound is desirably administered orally at a single dose of about 0.02 to 10 mg/kg, preferably about 0.02 to 2 mg/kg, more preferably about 0.04 to 0.8 mg/kg, or intravenously at a single dose of about 0.002 to 1 mg/kg, preferably about 0.02 to 1 mg/kg, more preferably about 0.02 to 0.2 mg/kg, about once to three times, preferably once to twice daily, according to the conditions being treated.

The starting compounds (III), (V), (VI), (VII) and (VIII) of this invention can be easily produced, for example, by the methods as illustrated in the following reaction schema:

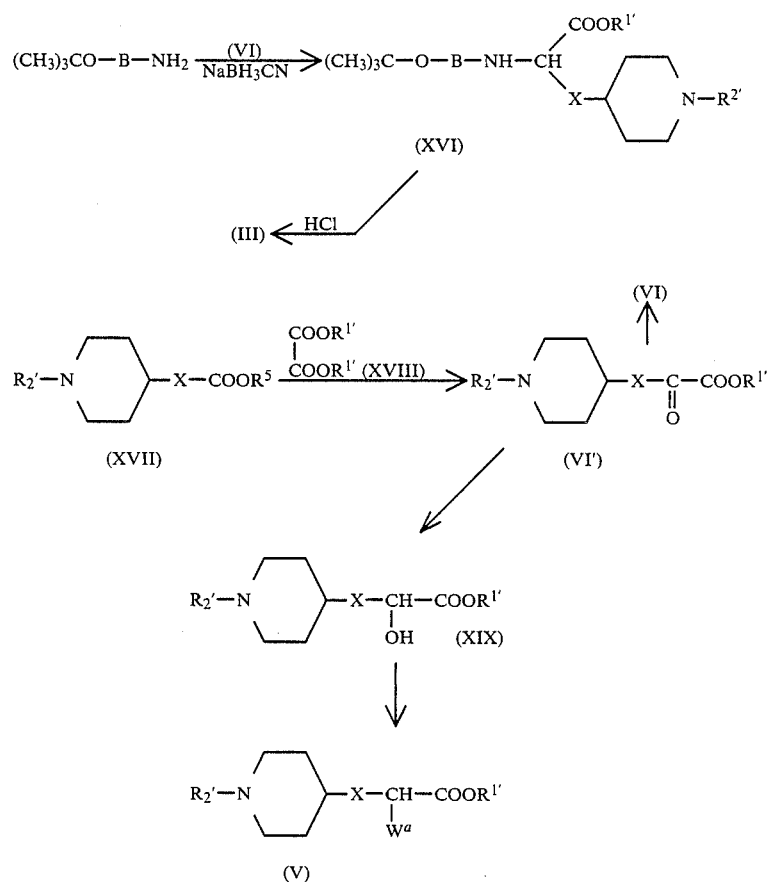

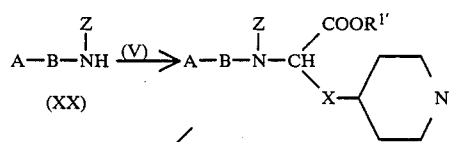

(XX) → (XXI) → (VII)

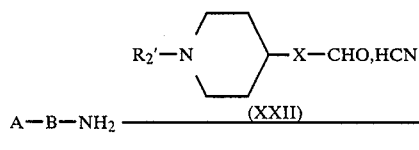

(IV) → (XXII) → (VIII)

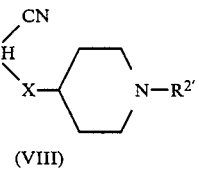

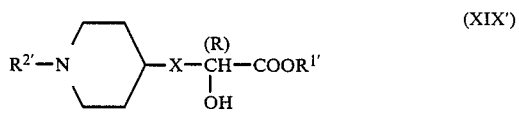

(XIX')

In the above reaction schema, $R^5$ is lower-($C_{1-4}$)-alkyl or aralkyl [e.g., phenyl-lower-($C_{1-4}$)-alkyl], and other symbols are as defined hereinbefore.

Referring in more detail to the process for producing the compound (III) as illustrated in the above reaction schema, an α-amino acid tert-butyl ester (XV) being used as a starting compound is reacted with a compound (VI') under reductive conditions to produce a compound (XVI), followed by treatment of (XVI) with an acid (e.g., hydrogen chloride) to give the compound (III).

In the processes for producing the compounds (V) and (VI), a compound (XVII) and a compound (XVIII) are subjected to condensation in the presence of a base, such as sodium ethoxide, followed by heating in aqueous dimethylsulfoxide in the presence of lithium chloride, etc. to yield a compound (VI'). The compound (VI) can be easily obtained by hydrolysis, ester exchange, etc. of the compound (VI').

The compound (XIX) can be produced by subjecting the compound (VI') to a per se known reductive reaction. The reductive reaction includes, for example, catalytic reduction; reduction with a metal hydride compound such as lithium borohydride, sodium borohydride or sedium cyanoborohydride; reduction with metallic sodium, metallic magnesium, etc. and an alcohol; reduction with a metal such as iron or zinc and an acid; and electrolytic reduction. The compound (V) can be produced, for example, by subjecting the compound (XIX) to a per se known halogenation or sulfonylation reaction.

A single isomer of the compound (I) can be produced by subjecting the compound (VI') to an asymmetric reduction reaction and subjecting the single isomer of the compound (XIX) obtained to a per se known halogenation or sulfonylation reaction. The asymmetric reduction reaction includes, for example, a reduction with a microorganism or its reducing enzyme, catalytic reduction with a catalyst ornamented by an asymmetric ligand and reduction with a metal hydride compound ornamented by an asymmetric ligand.

The present invention also provides a method for asymmetric synthesis of a compound of the formula wherein R represents R-configuration and other symbols are as defined hereinbefore, which comprises subjecting the compound (VI') to an asymmetric reduction reaction.

The microorganism or its reducing enzyme used for the present invention includes all microorganisms or their reducing enzymes having ability to asymmetrically reduce the compound (VI') to yield the compound (XIX'), but Baker's yeast is preferred, among others.

As the reaction mixture used for the present invention, an aqueous solution (inclusive of a buffer) of pH 5 to 7 containing about 1–30 g/l of the compound (VI') is preferable. The aqueous solution may contain about 0–100 ml/l of an organic solvent such as alcohol (e.g. methanol, ethanol).

In case that the reducing enzyme is used, it is preferable that an amount of the enzyme equal to asymmetrically reduce the compound (VI') or an excess of the enzyme is added and then that the reaction is carried out for about 0.5–24 hours.

In case that Baker's yeast, among the microorganisms, is used, it is preferable that 1 to 500 grams, preferably about 1 to 50 gramms, of Baker's yeast per gram of the compound (VI') is added and then that the reaction is carried out at 15° to 40° C., preferably 25° to 35° C. for 1 hour to 1 week. In case of use of a microorganism other than Baker's yeast, the reaction can be conducted in the manner similar to that of Baker's yeast. As a carbon source in the asymmetric reduction reaction using a microorganism, it is preferred that a sugar such as sucrose or glucose is added to the reaction mixture. If necessary, such substances as Bactotrypton, yeast extract, Casamino Acids and ammonium sulfate.

After the reaction, the compound (XIX) can be extracted with ethyl acetate, ether, alcohol, etc. without disrupting the cells or after the cells are disrupted by a surface active agent, lysozyme or mechanical distruct using glass beads. The compound (XIX) after the asymmetic reduction reaction using a reducing enzyme can also be extracted in a similar manner as mentioned above.

Among the compounds (VI') used for the asymmetric reduction reaction, the compound of the formula (VI') wherein $R^{1'}$ is lower ($C_{1-4}$) alkyl, $R^{2'}$ is phenyl-lower ($C_{1-4}$) alkoxycarbonyl such as benzyloxycarbonyl and X is tetramethylene.

The compound (VII) can be obtained by reacting the derivative (XX) having an amino group protected for example with the compound (V) to derive into a compound (XXI) and converting the compound (XXI). In the process for producing the compound (VIII), the compounds (IV) and (XXII), and hydrogen cyanide being used as starting compounds are treated in accordance with the known Strecker reaction to give the compound (VIII).

The compounds (II), (IV) and (XX) can be produced by the methods, or methods similar thereto, as described in the literature [e.g., Biochemical and Biophysical Research Communications, 117, 108 (1983): Federation of European Biochemical Societies, 165, 201 (1984): Journal of Medicinal Chemistry, 26, 1267 (1983): Tetrahedron Letters, 24, 5339 (1983): Tetrahedron Letters, 25, 4479 (1984): Tetrahedron Letters, 25, 4483 (1984): Japanese Unexamined Patent Publication No. 192395/1982: Japanese Unexamined Patent Publication No. 55451/1983; Japanese Unexamined Patent Publication No. 231052/1984: Japanese Unexamined Patent Publication No. 153769/1980: Japanese Unexamined Patent Publication No. 188857/1983: Japanese Unexamined Patent Publication No. 203050/1982: Japanese Unexamined Patent Publication No. 88165/1982: Japanese Unexamined Patent Publication No. 147257/1980: Japanese Unexamined Patent Publication No. 206387/1984: Japanese Unexamined Patent Publication No. 59175/1980: Japanese Unexamined Patent Publication No. 130268/1984: Japanese Unexamined Patent Publication No. 172367/1983: Japanese Unexamined Patent Publication No. 29686/1984: Japanese Unexamined Patent Publication No. 118766/1984: Japanese Unexamined Patent Publication No. 134765/1984: Japanese Unexamined Patent Publication No. 177967/1983: Japanese Unexamined Patent Publication No. 177968/1983: Japanese Unexamined Patent Publication No. 45155/1980: Japanese Unexamined Patent Publication No. 27199/1980: Japanese Unexamined Patent Publication No. 101463/1984: European Patent Application laid open No. 68173: Britisih Patent Application laid open No. 2095682: European Patent Application laid open No. 51391: European Patent Application laid open No. 57998: South African Republic Patent No. 836736].

Also, the compounds (V), (VI), (XVII) and (XXII) can be produced, for example, by the methods, or methods similar thereto, as described in U.S. patent application Ser. Nos. 637,620 filed on Aug. 3, 1984 and 691,005 filed on Jan. 14, 1985.

The following Examples are illustrating this invention but this invention is not limited to them.

EXAMPLE 1

A solution of 0.6 g of sodium cyanoborohydride in 50 ml of ethanol is added dropwise to a stirred mixture of 2 g of N-(L-alanyl)-N-(2-indanyl)glycine tert-butyl ester·oxalate, 0.78 g of sodium acetate, 0.58 g of acetic acid, 10 g of molecular sieves 3A, 3.6 g of ethyl 6-(1-benzyloxycarbonyl-4-piperidyl)-2-oxohexanoate and 50 ml of ethanol at room temperature over a period of 3 hours. The reaction solution is allowed to stand overnight and filtered, and the filtrate is concentrated under reduced pressure. The residue is diluted with 50 ml of water and extracted with 200 ml of ethyl acetate. The extract is dried and concentrated under reduced pressure. The resulting oily material is separated and purified by silica gel column chromatography (hexane:ethyl acetate=1:1 to 2:3), whereby the first fraction yields 0.35 g of N-[N-[(R)-5-(1-benzyloxycarbonyl-4-piperidyl)-1-ethoxycarbonylpentyl]-L-alanyl]-N-(indan-2-yl)glycine tert-butyl ester as a colorless oil.

IR $\nu_{max}^{neat}$cm$^{-1}$: 3320 (NH): 1730, 1690, 1650(C=O). Mass spectrum (m/e): 677(M$^+$) NMR spectrum $\delta$ (in CDCl$_3$): 7.3(5H,phenyl proton of benzyloxycarbonyl group), 7.2(4H,phenyl proton of indanyl group), 5.1(2H,methylene proton of benzyloxycarbonyl group), 1.4 (9H,methyl proton of tert-butyl group).

The subsequent second fraction provides 0.4 g of N-[N-[(S)-5-(1-benzyloxycarbonyl-4-piperidyl)-1-ethoxycarbonylpentyl]-L-alanyl]-N-(indan-2-yl)glycine tert-butyl ester as a colorless oil.

IR $\nu_{max}^{neat}$cm$^{-1}$: 3320(NH): 1760, 1690, 1640(C=O) Mass spectrum (m/e): 677(M$^+$) NMR spectrum $\delta$ (in CDCl$_3$): 7.3(5H,pehnyl proton of benzyloxycarbonyl group), 7.1(4H, phenyl proton of indanyl group), 5.1(methylene proton of benzyloxycarbonyl group), 1.4(methyl proton of tert-butyl group).

EXAMPLE 2

In 2 ml of acetic acid is dissolved 0.35 g of N-[N-[(R)-5-(1-benzyloxycarbonyl-4-piperidyl)-1-ethoxycarbonylpentyl]-L-alanyl]-N-(indan-2-yl)glycine tert-butyl ester, and 2 ml of 30% hydrogen bromide-acetic acid solution is added to the solution, followed by standing at room temperature for 1 hour. 50 ml of ethyl ether is added to the reaction mixture, followed by shaking, and the supernatant layer is removed by decantation. The colorless precipitate is rinsed with ethyl ether and dried under reduced pressure to give 0.3 g of N-[N-[(R)-1-ethoxycarbonyl-5-(4-piperidyl)pentyl]-L-alanyl]-N-(indan-2-yl)glycine·dihydrobromide as a colorless powder.

Elemental analysis for $C_{27}H_{41}N_3O_5 \cdot 2HBr \cdot 4H_2O$; Calcd.: C, 44.94; H, 7.13; N, 5.82; Found: C, 45.33; H, 6.97; N, 5.72; $[\alpha]_D - 7.9°$ (in methanol); SIMS spectrum (m/e): 488(MH$^+$).

EXAMPLE 3

In 2 ml of acetic acid is dissolved 0.4 g of N-[N-[(S)-5-(1-benzyloxycarbonyl-4-piperidyl)-1-ethoxycarbonylpentyl]-L-alanyl]-N-(indan-2-yl)glycine tert-butyl ester, and 2 ml of 30% hydrogen bromide-acetic acid solution is added to the solution, followed by standing at room temperature for 1 hour. 50 ml of ethyl ether is added to the reaction mixture, followed by shaking, and the supernatant layer is removed by decantation. The colorless precipitate is rinsed with ethyl ether and dried under reduced pressure to give 0.3 g of N-[N-[(S)-1-ethoxycarbonyl-5-(4-piperidyl)pentyl]-L-alanyl]-N-(indan-2-yl)glycine dihydrobromide as a colorless powder.

Elemental analysis for $C_{27}H_{41}N_3O_5 \cdot 2HBr \cdot 3H_2O$; Calcd.: C, 46.09; H, 7.01; N, 5.97; Found: C, 46.19; H, 6.95; N, 5.91; $[\alpha]_D + 2.6°$ (in methanol); SIMS spectrum (m/e): 488(MH$^+$).

EXAMPLE 4

In 210 ml of tetrahydrofuran is dissolved 26.1 g of N-benzyloxycarbonyl-L-alanine, and a solution of 16.4 ml of triethylamine in 20 ml of tetrahydrofuran is added dropwise to the solution at the temperature below $-10°$ C. with stirring. Then, a solution of 11.2 ml of ethyl chlorocarbonate in 20 ml of tetrahydrofuran is added dropwise to the solution. After stirring for 20 minutes, a solution of 15.4 g of L-proline tert-butyl ester in 102 ml of chloroform is added dropwise to the mixture at the temperature below −10° C. over a period of 48 minutes. After the addition is completed, stirring is continued for 1 hour under cooling and for 1.5 hours at room temperature. The reaction solution is poured into 600 ml of ice-water, and the chloroform layer is separated and concentrated under reduced pressure. The residue is dissolved in 304 ml of ethyl acetate, and the solution is washed with 1N aqueous sodium hydroxide, saturated aqueous sodium chloride, 20% aqueous phosphoric acid and saturated aqueous sodium chloride, successively. The ethyl acetate layer is dried over anhydrous magnesium sulfate, and concentrated under reduced pressure to give 33.8 g of N-(N-benzyloxycarbonyl-L-alanyl)-L-proline tert-butyl ester as an oil. This product is dissolved in 304 ml of methanol containing 8.12 g of oxalic acid, and 10% palladium-carbon (50% wet, 3.6 g) are added to the solution to conduct catalytic reduction at ambient temperature and under atmospheric pressure. The catalyst is filtered off, and the filtrate is concentrated under reduced pressure. 400 ml of ethyl ether is added to the residue, and the crystals which separate out are collected by filtration to give 20.2 g of N-(L-alanyl)-L-proline tert-butyl ester·oxalate as a colorless powder.

$[\alpha]_D^{24} -84.1°$ (c=1, in methanol); Elemental analysis, for $C_{12}H_{22}N_2O_3 \cdot C_2H_2O_4 \cdot 1/2H_2O$; Calcd.: C, 49.25; H, 7.38; N, 8.21; Found: C, 48.95; H, 6.94; N, 8.05.

EXAMPLE 5

A solution of 0.57 g of sodium cyanoborohydride in 40 ml of ethanol is added dropwise to a stirred mixture of 2 g of N-(L-alanyl)-L-proline tert-butyl ester. oxalate, 1 g of sodium acetate, 0.72 g of acetic acid, 10 g of molecular sieves 3A, 3.4 g of ethyl 6-(1-benzyloxycarbonyl-4-piperidyl)-2-oxohexanoate and 50 ml of ethanol at room temperature over a period of 2 hours. The reaction mixture is allowed to stand overnight and filtered, and the filtrate is concentrated under reduced pressure. The resulting oily material is purified by silica gel column chromatography (hexane:ethyl acetate=1:1 to hexane:acetone=1:1) to give 0.66 g of N-[N-[5-(1-benzyloxycarbonyl-4-piperidyl)-1-ethoxycarbonylpentyl]-L-alanyl]-L-proline tert-butyl ester as a colorless oil.

IR $\nu_{max}^{neat}$ cm$^{-1}$: 3325(NH): 1730, 1690, 1650(C=O). Mass spectrum (m/e): 601(M+); NMR spectrum δ (in CDCl$_3$): 7.3(5H,phenyl proton of benzyloxycarbonyl group), 5.1(2H,methylene proton of benzyloxycarbonyl group), 1.4(9H, methyl proton of tert-butyl group).

EXAMPLE 6

In 1.5 ml of acetic acid is dissolved 0.66 g of N-[N-[5-(1-benzyloxycarbonyl-4-piperidyl)-1-ethoxycarbonyl-pentyl]-L-alanyl]-L-proline tert-butyl ester, and 2 ml of 30% hydrogen bromide-acetic acid solution is added to the solution, followed by standing at room temperature for 1 hour. 50 ml of ethyl ether is added to the reaction solution, followed by shaking, and the precipitate is rinsed twice with 50 ml of ethyl ether. The resulting yellow, viscous material is dissolved in 5 ml of water, and the solution is extracted with 10 ml of ethyl acetate. The aqueous layer is lyophilized to give 0.4 g of N-[N-1-ethoxycarbonyl-5-(4-piperidyl)pentyl]-L-alanyl-L-proline·dihydrobromide.

Elemental analysis, for $C_{21}H_{37}N_3O_5 \cdot 2HBr \cdot 4H_2O$; Calcd.: C, 39.08; H, 7.34; N, 6.51; Found: C, 39.43; H, 7.10; N, 6.50.

EXAMPLE 7

In 20 ml of methanol is dissolved 0.4 g of N-[N-[(S)-5-(1-benzyloxycarbonyl-4-piperidyl)-1-ethoxycarbonyl-pentyl]-L-alanyl]-N-(indan-2-yl)glycine tert-butyl ester, and a catalytic reduction is carried out at ambient temperature and under atmospheric pressure using 10% palladium-carbon (50% wet, 0.4 g) as a catalyst. After stirring at room temperature for 4 hours, the catalyst is removed by filtration, and the filtrate is concentrated under reduced pressure to give 0.3 g of N-[N-[(S)-5-(4-piperidyl)-1-ethoxycarbonylpentyl]-L-alanyl]-N-(indan-2-yl)glycine tert-butyl ester as a colorless oil.

EXAMPLE 8

In 2 ml of acetic acid is dissolved 0.3 g of N-[N-[(S)-5-(4-piperidyl)-1-ethoxycarbonylpentyl]-L-alanyl]-N-(indan-2-yl)glycine tert-butyl ester, and 1 ml of hydrogen bromide-acetic acid solution is added to the solution, followed by standing at room temperature for 30 minutes. 50 ml of ethyl ether is added to the reaction solution, followed by shaking, and the supernatant layer is removed by decantation. The precipitate is collected and dried under reduced pressure to give 0.3 g of N-[N-[(S)-1-ethoxycarbonyl-5-(4-piperidyl)pentyl]-L-alanyl]-N-(indan-2-yl)glycine·dihydrobromide as a colorless powder.

EXAMPLE 9

In 6 ml of 1N aqueous sodium hydroxide is dissolved 0.25 g of N-[N-[(S)-1-ethoxycarbonyl-5-(4-piperidyl)-pentyl]-L-alanyl]-N-(indan-2-yl)glycine·dihydrobromide, and the solution is allowed to stand at room temperature for 30 minutes. The reaction solution is made weakly acidic with acetic acid and purified by column chromatography on Amberlite XAD-2 (0.1M aqueous ammonia-5% acetonitrile). The effluent is concentrated under reduced pressure and lyophilized to give 0.11 g of N-[N-[(S)-1-carboxy-5-(4-piperidyl)pentyl]-L-alanyl]-N-(indan-2-yl)glycine as a colorless powder.

$[\alpha]_D^{24} +6.1°$ (c=0.4 in water); Elemental analysis, for $C_{25}H_{37}N_3O_5 \cdot 2H_2O$; Calcd.: C, 60.59; H, 8.34; N, 8.48; Found: C, 60.37; H, 7.99; N, 8.70; SIMS spectrum (m/e): 460(MH+).

EXAMPLE 10

In 20 ml of methanol is dissolved 0.55 g of N-[N-[(S)-5-(1-benzyloxycarbonyl-4-piperidyl)-1-ethoxycarbonyl-pentyl]-L-alanyl]-N-(indan-2-yl)glycine tert-butyl ester, and 5 ml of 1N aqueous sodium hydroxide is added dropwise to the solution over a period of 5 minutes. After stirring at room temperature for 1 hour, another 2 ml of 1N aqueous sodium hydroxide is added dropwise to the mixture over a period of 5 hours. After 2 ml of water is added dropwise over a period of 2 hours, 10 ml of water is added to the reaction solution, and the mixture is extracted with 10 ml of n-hexane. The aqueous layer is made weakly acidic with 1N hydrochloric acid, and extracted with 50 ml of ethyl acetate. The extract is washed with water, dried over anhydrous magnesium sulfate and concentrated under reduced pressure to give 0.5 g of N-[N-[(S)-5-(1-benzyloxycarbonyl-4-piperidyl)-

1-carboxypentyl]-L-alanyl]-N-(indan-2-yl)glycine tert-butyl ester as a colorless oil.

SIMS spectrum (m/e): 650 (MH+).

EXAMPLE 11

In 20 ml of methanol is dissolved 0.5 g of N-[N-[(S)-5-(1-benzyloxycarbonyl-4-piperidyl)-1-carboxypentyl]-L-alanyl]-N-(indan-2-yl)glycine tert-butyl ester, and a catalytic reduction is carried out at ambient temperature and under atmospheric pressure using 10% palladium-carbon (50% wet., 0.5 g) as a catalyst. After stirring at room temperature for 4 hours, the catalyst is filtered off, and the filtrate is concentrated under reduced pressure to give 0.28 g of N-[N-[(S)-5-(4-piperidyl)-1-carboxypentyl]-L-alanyl]-N-(indan-2-yl)glycine tert-butyl ester as a colorless powder.

Mass spectrum (m/e): 515(M+).

EXAMPLE 12

In a mixture of 2 ml of acetic acid and 2 ml of ethyl acetate is dissolved 0.28 g of N-[N-[(S)-5-(4-piperidyl)-1-carboxypentyl]-L-alanyl]-N-(indan-2-yl)-glycine tert-butyl ester, and 5 ml of 5N hydrogen chloride-ethyl acetate solution is added to the solution, followed by standing at room temperature for 1 hour. 100 ml of ethyl ether is added to the reaction solution, and the precipitate which separates out is collected by filtration to give 0.22 g of N-[N-[(S)-1-carboxy-5-(4-piperidyl)pentyl]-L-alanyl]-N-(indan-2yl)glycine·dihydrochloride as a colorless powder.

EXAMPLE 13

A mixture of 5 g of L-alanine tert-butyl ester·oxalate, 11 g of ethyl 6-(1-benzyloxycarbonyl-4-piperidyl)-2-oxohexanoate, 1.6 g of sodium acetate, 1.2 g of acetic acid and 100 ml of ethanol is stirred at room temperature for 1 hour, and a solution of 1.9 g of sodium cyanoborohydride in 100 ml of ethanol is added dropwise to the mixture over a period of 4 hours. After stirring at room temperature overnight, 500 ml of water is added to the reaction mixture, and the mixture is extracted with 300 ml of ethyl acetate. The extract is washed with water, dried over anhydrous magnesium sulfate and concentrated under reduced pressure. The residue is separated and purified by silica gel column chromatography (hexane:acetone=4:1), whereby the first fraction yields 1.7 g of N-[(R)-5-(1-benzyloxycarbonyl-4-piperidyl)-1-ethoxycarbonylpentyl]-L-alanine tert-butyl ester as a colorless oil.

IR $\nu_{max}^{neat}$cm$^{-1}$: 3350(NH); 1730, 1700(C=O); Mass spectrum (m/e): 504(M+); NMR spectrum δ (in CDCl$_3$): 7.3(5H,phenyl proton of benzyloxycarbonyl group), 5.1(2H,s,methylene proton of benzyloxycarbonyl group), 1.45(9H,s,methyl proton of tert-butyl group).

The second fraction provides 1.5 g of N-[(S)-5-(1-benzyloxycarbonyl-4-piperidyl)-1-ethoxycarbonylpentyl]-L-alanine tert-butyl ester as a colorless oil.

IR $\nu_{max}^{neat}$cm$^{-1}$: 3350(NH); 1730, 1700(C=O); NMR δ (in CDCl$_3$): 7.2(5H,phenyl proton of benzyloxycarbonyl group), 5.1(2H,s,methylene proton of benzyloxycarbonyl group), 1.45(9H,s,methyl proton of tert-butyl group); Mass spectrum (m/e): 504(M+).

EXAMPLE 14

In 20 ml of 5N hydrogen chloride-ethyl acetate solution is dissolved 1.7 g of N-[(R)-5-(1-benzyloxycarbonyl-4-piperidyl)-1-ethoxycarbonylpentyl]-L-alanine tert-butyl ester, and the solution is allowed to stand at room temperature for 4 hours. 100 ml of ethyl ether is added to the reaction solution, and the colorless powder, which separates out, is collected by filtration to give 1.2 g of N-[(R)-5-(1-benzyloxycarbonyl-4-piperidyl)-1-ethoxycarbonylpentyl]-L-alanine·hydrochloride.

Elemental analysis, for $C_{24}H_{36}N_2O_6 \cdot HCl \cdot H_2O$; Calcd.: C, 57.31; H, 7.81; N, 5.57; Found: C, 56.91; H, 7.85; N, 5.92; $[\alpha]_D^{24}$ −9.9° (c=0.5, in methanol); Mass spectrum (m/e): 448(M+).

EXAMPLE 15

In 30 ml of 5N hydrogen chloride-ethyl acetate solution is dissolved 1.5 g of N-[(S)-5-(1-benzyloxycarbonyl-4-piperidyl)-1-ethoxycarbonylpentyl]-L-alanine tert-butyl ester, and the solution is allowed to stand at room temperature for 5 hours. The reaction solution is concentrated to dryness under reduced pressure, and the residue is rinsed with ethyl ether and dried under reduced pressure to give 1.15 g of N-[(S)-5-(1-benzyloxycarbonyl-4-piperidyl)-1-ethoxycarbonylpentyl]-L-alanine·hydrochloride as a colorless gum.

Elemental analysis, for $C_{24}H_{36}N_2O_6 \cdot HCl \cdot H_2O$; Calcd.: C, 57.31; H, 7.81; N, 5.57; Found: C, 57.19; H, 8.06; N, 5.61; $[\alpha]_D^{24}$ +12.7° (c=0.5, in methanol); Mass spectrum (m/e): 448(M+).

EXAMPLE 16

In 2 ml of N,N-dimethylformamide are dissolved 25 mg of N-(2-indanyl)glycine tert-butyl ester and 50 mg of N-[(R)-5-(1-benzyloxycarbonyl-4-piperidyl)-1-ethoxycarbonylpentyl]-L-alanine·hydrochloride, and 0.1 ml of diethyl phosphorocyanidate is added to the solution under ice-cooling with stirring. After stirring for 30 minutes, 0.1 ml of triethylamine is added to the mixture, followed by stirring under ice-cooling for 30 minutes and then stirring at room temperature for 30 minutes. 50 ml of water is added to the reaction solution, and the mixture is extracted with 30 ml of ethyl acetate. The extract is dried over anhydrous magnesium sulfate and concentrated under reduced pressure. The residue is purified by silica gel column chromatography (hexane:ethyl acetate=1:1) to give 30 mg of N-[N-(R)-5-(1-benzyloxycarbonyl-4-piperidyl)-1-ethoxycarbonylpentyl]-L-alanyl]-N-(indane-2-yl)glycine tert-butyl ester as a colorless oil.

EXAMPLE 17

In 2 ml of N,N-dimethylformamide are dissolved 25 mg of N-(2-indanyl)glycine tert-butyl ester and 50 mg of N-[(S)-5-(1-benzyloxycarbonyl-4-piperidyl)-1-ethoxycarbonylpentyl]-L-alanine·hydrochloride, and 0.1 ml of diethyl phosphorocyanidate is added to the solution under ice-cooling with stirring. After stirring for 30 minutes, 0.1 ml of triethylamine is added to the mixture, followed by stirring under ice-cooling for 30 minutes and then stirring at room temperature for 30 minutes. 50 ml of water is added to the reaction solution, and the mixture is extracted with 30 ml of ethyl acetate. The extract is dried over anhydrous magnesium sulfate and concentrated under reduced pressure. The residue is purified by silica gel column chromatography (hexane:ethyl acetate=1:1) to give 35 mg of N-[N-(S)-5-(1-benzyloxycarbonyl-4-piperidyl)-1-ethoxycarbonylpentyl]-L-alanyl]-N-(indan-2-yl)glycine tert-butyl ester as a colorless oil.

EXAMPLE 18

In 20 ml of N,N-dimethylformamide are dissolved 0.4 g of tert-butyl (S)-1,2,3,4-tetrahydroisoquinoline-3-carboxylate hydrochloride and 0.4 g of N-[(S)-5-(1-benzyloxycarbonyl-4-piperidyl)-1-ethoxycarbonylpentyl]-L-alanine·hydrochloride, and 0.4 ml of diethyl phosphorocyanidate is added dropwise to the solution under ice-cooling with stirring. After stirring for 30 minutes, 0.4 ml of triethylamine is added dropwise to the mixture, followed by stirring under ice-cooling for 1 hour and then at room temperature for 30 minutes. 200 ml of water is added to the reaction mixture, and the mixture is extracted with 200 ml of ethyl acetate. The extract is washed with 5% aqueous phosphoric acid and water, successively, dried over anhydrous magnesium sulfate and concentrated under reduced pressure. The residue is purified by silica gel column chromatography (hexane:acetone=2:1) to give 0.37 g of tert-butyl (S)-2-[N-(S)-5-(1-benzyloxycarbonyl-4-piperidyl)-1-ethoxycarbonylpentyl]-L-alanyl]-1,2,3,4-tetrahydroisoquinoline-3-carboxylate as a colorless oil.

IR $\nu_{max}^{neat}$cm$^{-1}$: 1730, 1690, 1640(C=0); NMR $\delta$ (in CDCl$_3$): 7.0–7.3(9H,phenyl proton), 5.1(2H, s, methylene proton of benzyloxycarbonyl group), 1.2(9H,s,methyl proton of tert-butyl group); Mass spectrum (m/e): 663(M+).

EXAMPLE 19

In 1 ml of acetic acid is dissolved 0.37 g of tert-butyl (S)-2-[N-(S)-5-(1-benzyloxycarbonyl-4-piperidyl)-1-ethoxycarbonylpentyl]-L-alanyl]-1,2,3,4-tetrahydroisoquinoline-3-carboxylate, and 2 ml of 30% hydrogen bromide-acetic acid solution is added to the solution, followed by standing at room temperature for 1 hour. 50 ml of ethyl ether is added to the reaction solution, followed by shaking. After standing, the supernantant layer is removed by decantation. The precipitate is collected and dried under reduced pressure to give 0.36 g of (S)-2-[N-[(S)-1-ethoxycarbonyl-5-(4-piperidyl)pentyl-L-alanyl]-1,2,3,4-tetrahydroisoquinoline-3-carboxylic acid·dihydrobromide as a colorless powder.

$[\alpha]_D^{25}$+5.8° (c=0.4, in MeOH); SIMS spectrum (m/e): 474(MH+); 512(M+K)+ (addition of KI).

EXAMPLE 20

In 8 ml of 1N aqueous sodium hydroxide is dissolved 0.3 g of (S)-2-[N-[(S)-1-ethoxycarbonyl-5-(4-piperidyl)pentyl]-L-alanyl]-1,2,3,4-tetrahydroisoquinoline-3-carboxylic acid·dihydrobromide, and the solution is allowed to stand at room temperature for 1 hour. The reaction solution is made acidic with 1 ml of acetic acid, and then purified by Amberlite XAD-2 column chromatography (0.1M aqueous ammonia-5% acetonitrile). The effluent is concentrated under reduced pressure, and lyophilized to give 0.16 g of (S)-2-[N-[(S)-1-carboxy-5-(4-piperidyl)pentyl]-L-alanyl]-1,2,3,4-tetrahydroisoquinoline-3-carboxylic acid as a colorless powder.

SIMS spectrum (m/e): 446(MH+); 484(M+K)+, 522(M+2K)+ (addition of KI).

EXAMPLE 21

In 30 ml of N,N-dimethylformamide are dissolved 2.4 g of L-proline tert-butyl ester and 5.87 g of N$^\alpha$-benzyloxycarbonyl-N$^\epsilon$-tert-butoxycarbonyl-L-lysine, and 3 g of diethyl phosphorocyanidate is added dropwise to the solution under ice-cooling. After stirring for 30 minutes, a solution of 1.42 g of triethylamine in 5 ml of N,N-dimethylformamide is added to the mixture, followed by stirring under ice-cooling for 1 hour and then at room temperature for 2 hours. 500 ml of water is added to the reaction mixture, and the mixture is extracted with 300 ml of ethyl acetate. The extract is washed with aqueous dilute phosphoric acid, 0.1N aqueous sodium hydroxide and water, successively, dried over anhydrous magnesium sulfate and concentrated under reduced pressure. The resulting oily material is purified by silica gel column chromatography (hexane:ethyl acetate=2:1 to 1:1) to give 5.5 g of N-(N$^\alpha$-benzyloxycarbonyl-N$^\epsilon$-tert-butoxycarbonyl-L-lysyl)-L-proline tert-butyl ester as a colorless oil.

Mass spectrum (m/e): 533(M+).

In 50 ml of methanol is dissolved 2.5 g of this product, and a catalytic reduction is carried out at ambient temperature and under atmospheric pressure using 10% palladium-carbon (50% wet, 1 g) as a catalyst. After the absorption of hydrogen is observed to stop, the catalyst is removed by filtration, and the filtrate is concentrated under reduced pressure. A solution of 0.5 g of oxalic acid in 50 ml of ethyl ether is added to the resulting oily material to give 1.5 g of N-(N$^\epsilon$-tert-butoxycarbonyl-L-lysyl)-L-proline tert-butyl ester·oxalate as colorless scales. m.p. 154°–156° C.

Elemental analysis, for C$_{20}$H$_{37}$N$_3$O$_5$·(COOH)$_2$·H$_2$O; Calcd.: C, 52.05; H, 8.14; N, 8.28; Found: C, 51.93; H, 7.67; N, 8.10.

EXAMPLE 22

A mixture of 0.4 g of N-(N$^\epsilon$-tert-butoxycarbonyl-L-lysyl)-L-proline tert-butyl ester·oxalate, 1.5 g of ethyl 6-(1-benzyloxy-4-piperidyl)-2-oxohexanoate, 0.07 g of sodium acetate, 0.05 g of acetic acid and 30 ml of ethanol is stirred at room temperature for 30 minutes, and a solution of 0.05 g of sodium cyanoborohydride in 10 ml of ethanol is added dropwise to the mixture at room temperature over a period of 4 hours. Furthermore, a solution of 0.2 g of sodium cyanoborohydride in 40 ml of ethanol is added dropwise to the mixture over a period of 3 hours, followed by stirring overnight. 500 ml of water is added to the reaction solution, and the mixture is extracted with ethyl acetate. The extract is washed with water, dried over anhydrous magnesium sulfate and concentrated under reduced pressure. The residue is purified by silica gel column chromatography (hexane:acetone=3:1) to give 0.43 g of N-[N$^\alpha$-[5-(1-benzyloxycarbonyl-4-piperidyl)-1-ethoxycarbonylpentyl]-N$^\epsilon$-tert-butoxycarbonyl-L-lysyl]-L-proline tert-butyl ester as a colorless oil.

IR $\nu_{max}^{neat}$cm$^{-1}$: 3350(NH); 1730, 1700, 1630(C=0); NMR spectrum $\delta$ (in CDCl$_3$): 7.25(5H,pehnylproton of benzyloxycarbonyl group), 5.1(2H,s,methylene proton of benzyloxycarbonyl group), 1.4(18H,s,methyl proton of tert-butyl group); Mass spectrum (m/e): 758(M+).

EXAMPLE 23

In 1 ml of acetic acid is dissolved 0.43 g of N-[N$^\alpha$-[5-(1-benzyloxycarbonyl-4-piperidyl)-1-ethoxycarbonylpentyl]-N$^\epsilon$-tert-butoxycarbonyl-L-lysyl]-L-proline tert-butyl ester, and 2 ml of 30% hydrogen bromide-acetic acid solution is added to the solution, followed by standing at room temperature for 1 hour. 50 ml of ethyl ether is added to the reaction solution, followed by shaking, and the supernatant layer is removed by decantation. The precipitate is collected and dried under reduced pressure to give 0.3 g of N-[N$^\alpha$-[1-ethoxycarbonyl-5-(4-piperidyl)pentyl]-L-lysyl]-L-proline·trihydrobromide as a colorless powder.

Elemental analysis, for $C_{24}H_{44}N_4O_5 \cdot 3HBr \cdot 4H_2O$; Calcd.: C, 36.79; H, 7.08; N, 7.15; Found: C, 37.27; H, 7.07; N, 6.72; SIMS spectrum (m/e): 469(MH+), 507(M+K)+, KI added.

EXAMPLE 24

In an aqueous solution (150 ml) of 6.1 g of sodium carbonate is dissolved 11.7 g of 2-amino-4-(2-nitrophenyl)-butyric acid, and 15 g of N-ethoxycarbonylphthalimide is added to the solution under stirring. After stirring at room temperature overnight, the insoluble material is removed by filtration, and the filtrate is made weakly acidic with concentrated hydrochloric acid. The viscous material, which separates out, is admixed with 50 ml of ethanol, followed by stirring, whereby there separate out crystals. The crystals are collected by filtration and dried to give 13 g of 4-(2-nitrophenyl)-2-phtalimidobutyric acid as colorless crystals. m.p. 177°–179° C.

Elemental analysis, for $C_{18}H_{14}N_2O_6$; Calcd.: C, 61.02; H, 3.98; N, 7.91; Found: C, 61.04; H, 3.98; N, 7.82; IR spectrum $\nu_{max}^{nujol}cm^{-1}$: 1780, 1730, 1720(C=O).

EXAMPLE 25

In 300 ml of methanol, 13 g of 4-(2-nitrophenyl)-2-phthalimidobutyric acid is catalytically reduced at ambient temperature and under atmospheric pressure with use of 3 g of 5% palladium-carbon as a catalyst. After the calculated amount of hydrogen is absorbed, the insoluble material is separated by filtration, and washed four times with 300 ml of acetone. The acetone washings and the methanol portion are combined and concentrated under reduced pressure. The residue is admixed with 50 ml of ethanol, and the crystals which separate out are collected by filtration to give 10.1 g of 4-(2-aminophenyl)-2-phthalimidobutyric acid as yellow prisms. m.p. 198°–203° C. (decomp.).

Elemental analysis, for $C_{18}H_{16}N_2O_4$; Calcd.: C, 66.66; H, 4.97; N, 8.64; Found: C, 66.16; H, 4.97; N, 8.71; IR spectrum $\nu_{max}^{nujol}cm^{-1}$: 3380, 3300(NH); 1770, 1710(C=O).

EXAMPLE 26

In 80 ml of N,N-dimethylformamide is dissolved 10 g of 4-(2-aminophenyl)-2-phthalimidobutyric acid, and 6.7 g of diethyl phosphorocyanidate is added dropwise to the solution under ice-cooling with stirring. After the addition is complete, stirring is continued for 15 minutes, and 3.1 g of triethylamine is added dropwise to the mixture under ice cooling, followed by stirring under ice-cooling for 45 minutes and then at room temperature for 30 minutes. The reaction solution is diluted with 200 ml of water, followed by stirring for 1 hour, and the crystals, which separate out, are collected by filtration, dried and added to 100 ml of ethanol, followed by heating. After the solution is concentrated to about half of the original volume, the colorless prisms which separate out are collected by filtration to give 8.3 g of 3-phthalimido-1,3,4,5-tetrahydro-1-benzazepin-2-one. m.p. 261°–263° C.

Elemental analysis, for $C_{18}H_{14}N_2O_3$; Calcd.: C, 70.58; H, 4.61; N, 9.15; Found: C, 70.28; H, 4.66; N, 9.12; IR spectrum $\nu_{max}^{nujol}cm^{-1}$: 1770, 1710, 1680(C=O).

EXAMPLE 27

In 50 ml of N,N-dimethylformamide is dissolved 8.3 g of 3-phthalimido-1,3,4,5-tetrahydro-1-benzazepin-2-one, and 6.1 g of tert-butyl chloroacetate, 8 g of potassium carbonate and 2 g of potassium iodide are added to the solution, followed by stirring at room temperature overnight. The reaction solution is diluted with 300 ml of water, extracted with 500 ml of methylene chloride. The extract is washed with water, 1N hydrochloric acid and water, successively, dried over anhydrous magnesium sulfate and concentrated under reduced pressure. 50 ml of ethanol is added to the residue, whereby there separates out tert-butyl 2-oxo-3-phthalimido-2,3,4,5-tetrahydro-1H-1-benzazepine-1-acetate as crystals. Collection by filtration yields 10.2 g of colorless prisms, m.p. 203°–205° C.

Elemental analysis, for $C_{24}H_{24}N_2O_5$; Calcd.: C, 68.56; H, 5.75; N, 6.66; Found: C, 68.27; H, 5.71; N, 6.38; IR spectrum $\nu_{max}^{nujol}cm^{-1}$: 1770, 1740, 1720, 1680(C=O).

EXAMPLE 28

To 100 ml of ethanol is added 10 g of tert-butyl 2-oxo-3-phthalimido-2,3,4,5-tetrahydro-1H-1-benzazepine-1-acetate, and 5 g of hydrazine hydrate is added to the mixture, followed by refluxing for 2 hours. The reaction mixture is concentrated under reduced pressure, and 300 ml of water is added to the residue, followed by extraction with 200 ml of ethyl acetate. The extract is washed with 1N aqueous sodium hydroxide and water, successively, dried over anhydrous magnesium sulfate and concentrated under reduced pressure. The crystals, which separate out, are treated with a mixture of ether and petroleum ether and collected by filtration to give 6 g of tert-butyl 3-amino-2-oxo-2,3,4,5-tetrahydro-1H-1-benzazepine-1-acetate as colorless prisms. m.p. 121°–122° C.

Elemental analysis, for $C_{16}H_{22}N_2O_3$; Calcd.: C, 66.18; H, 7.64; N, 9.65; Found: C, 66.46; H, 7.68; N, 9.63; IR spectrum $\nu_{max}^{nujol}cm^{-1}$: 1735, 1665 (C=O).

EXAMPLE 29

A mixture of 1.75 g of tert-butyl 3-amino-2-oxo-2,3,4,5-tetrahydro-1H-1-benzazepine-1-acetate and 1.1 g of ethyl 6-(1-benzyloxycarbonyl-4-piperidyl)-2-methanesulfonyloxyhexanoate is heated at 90° C. for 24 hours. After cooling, the reaction solution is diluted with 200 ml of ethyl acetate, and the resulting solution is washed with 30 ml of 5% aqueous phosphoric acid and water, successively, and dried over anhydrous magnesium sulfate. After the solvent is distilled off under reduced pressure, the residue is separated and purified by silica gel column chromatography (hexane:ethyl acetate=2:1), whereby the first fraction yields 0.8 g of tert-butyl 3(RS)-[5-(1-benzyloxycarbonyl-4-piperidyl)-1(SR)-ethoxycarbonylpentyl]amino-2-oxo-2,3,4,5-tetrahydro-1H-1-benzazepine-1-acetate as a colorless oil.

IR spectrum $\nu_{max}^{neat}cm^{-1}$: 3310(NH): 1730, 1690, 1665(C=O); Mass spectrum (m/e): 649(M+);

From the subsequent fraction, 0.7 g of tert-butyl 3-(RS)-[5-(1-benzyloxycarbonyl-4-piperidyl)-1(RS)-ethoxycarbonylpentyl]amino-2-oxo-2,3,4,5-tetrahydro-1H-1-benzazepine-1-acetate is obtained as a colorless oil.

IR spectrum $\nu_{max}^{neat}cm^{-1}$: 3320(NH); 1730, 1690, 1660(C=O); Mass spectrum (m/e): 649(M+).

EXAMPLE 30

In 2 ml of acetic acid is dissolved 0.8 g of tert-butyl 3(RS)-[5-(1-benzyloxycarbonyl-4-piperidyl)-1(SR)-ethoxycarbonylpentyl]amino-2-oxo-2,3,4,5-tetrahydro-1H-1-benzazepine-1-acetate, and 2 ml of 30% aqueous hydrogen bromide-acetic acid solution is added to the solution, followed by standing at room temperature for 2 hours. The reaction solution is diluted with 200 ml of ethyl ether, and after the mixture is allowed to stand, the supernatant layer is removed by decantation. The precipitate is rinsed with 100 ml of ethyl ether and dried to give 3(RS)-[5-(4-piperidyl)-1(SR)-ethoxycarbonylpentyl]amino-2-oxo-2,3,4,5-tetrahydro-1H-1-benzazepine-1-acetic acid·hydrobromide. This product is dissolved in 20 ml of 1N aqueous sodium hydroxide and the solution is allowed to stand at room temperature for 1 hour, acidified with 2 ml of acetic acid and purified by XAD-2 column chromatography (methanol:-water=1:1). The effluent is concentrated under reduced pressure, and the crystals, which separate out, are rinsed with 50 ml of acetone and collected by filtration to give 0.33 g of 3(RS)-[5-(4-piperidyl)-1(SR)-carboxypentyl]amino-2-oxo-2,3,4,5-tetrahydro-1H-benzazepine-1-acetic acid as colorless prisms. m.p. 250°–260° C. (decomp.).

Elemental analysis, for $C_{23}H_{33}N_3O_5 \cdot H_2O$; Calcd.: C, 61.45; H, 7.85; N, 9.35; Found: C, 61.50; H, 7.55; N, 9.26; SIMS spectrum (m/e): 432(MH+); IR spectrum $\nu_{max}^{nujol}cm^{-1}$: 1660(C=0).

EXAMPLE 31

In 2 ml of acetic acid is dissolved 0.7 g of tert-butyl 3(RS)-[5-(1-benzyloxycarbonyl-4-piperidyl)-1(RS)-ethoxycarbonylpentyl]amino-2-oxo-2,3,4,5-tetrahydro-1H-1-benzazepine-1-acetate, and 2 ml of 30% hydrogen bromide-acetic acid solution is added to the solution, followed by standing at room temperature for 2 hours. The reaction solution is diluted with 100 ml of ethyl ether, and after the mixture is allowed to stand, the supernatant layer is removed by decantation. The precipitate is rinsed with 50 ml of ethyl ether and dried to give 3(RS)-[5-(4-piperidyl)-1(RS)-ethoxycarbonylpentyl]amino-2-oxo-2,3,4,5-tetrahydro-1H-1-benzazepine-1-acetic acid·hydrobromide. This product is dissolved in 20 ml of 1N aqueous sodium hydroxide, and the solution is allowed to stand at room temperature for 1 hour, made acidic with 2 ml of acetic acid and purified by XAD-2 column chromatography (methanol:-water=1:1). The effluent is concentrated under reduced pressure, and the crystals, which separate out, are rinsed with 50 ml of acetone and collected by filtration to give 0.22 g of 3(RS)-[5-(4-piperidyl)-1(RS)-carboxypentyl]amino-2-oxo-2,3,4,5-tetrahydro-1H-benzazepine-1-acetic acid as colorless prisms. m.p. 240°–260° C. (decomp.).

Elemental analysis, for $C_{23}H_{33}N_3O_5 \cdot H_2O$; Calcd.: C, 61.45; H, 7.85; N, 9.35; Found: C, 61.34; H, 7.50; N, 9.36; SIMS spectrum (m/e): 432(MH+); IR spectrum $\nu_{max}^{nujol}cm^{-1}$: 1670(C=0).

EXAMPLE 32

In 10 ml of N,N-dimethylformamide are dissolved 0.56 g of benzyl (S,S,S)-2-azabicyclo[3,3,0]octane-3-carboxylate·hydrochloride and 0.5 g of N-[(S)-5-(1-benzyloxycarbonyl-4-piperidyl)-1-ethoxycarbonylpentyl]-L-alanine·hydrochloride, and 0.3 g of triethylamine is added to the solution under ice-cooling with stirring, followed by addition of 0.5 ml of diethyl phosphorocyanidate. After stirring for 30 minutes, there is added to the mixture 0.1 g of triethylamine, followed by stirring for 30 minutes and at room temperature for 1 hour. The reaction mixture is diluted with 100 ml of water and extracted with 100 ml of ethyl acetate. The extract is washed with 5% aqueous phosphoric acid and water, successively, and dried over anhydrous magnesium sulfate. The solvent is distilled off under reduced pressure, and the residue is purified by silica gel column chromatography (hexane:acetone=3:1) to give 0.26 g of benzyl (S,S,S)-2-[N-[(S)-5-(1-benzyloxycarbonyl-4-piperidyl)-1-ethoxycarbonylpentyl]-L-alanyl]-2-azabicyclo-[3,3,0]octane-3-carboxylate as a colorless oil.

IR spectrum $\nu_{max}^{neat}cm^{-1}$: 1740, 1690, 1640(C=0); Mass spectrum (m/e): 675(M+).

EXAMPLE 33

In 50 ml of ethanol is dissolved 0.26 g of benzyl (S,S,S)-2-[N-[(S)-5-(1-benzyloxycarbonyl-4-piperidyl)-1-ethoxycarbonylpentyl]-L-alanyl]-2-azabicyclo[3,3,-0]octane-3-carboxylate, and a catalytic reduction is carried out at ambient temperature and under atmospheric pressure using 0.2 g of 10% palladium-carbon (50% wet) as a catalyst. After the reaction is allowed to proceed for 4 hours, the catalyst is filtered off, and the filtrate is concentrated under reduced pressure to give (S,S,S)-2-[N-[(S)-5-(4-piperidyl)-1-ethoxycarbonylpentyl]-L-alanyl]-2-azabicyclo[3,3,0]octane-3-carboxylic acid as a colorless oil. This product is dissolved in 5 ml of 1N aqueous sodium hydroxide, and the solution is allowed to stand at room temperature for 1 hour, made weakly acidic with 1 ml of acetic acid and purified by XAD-2 column chromatoraphy (0.15M aqueous ammonia-5% acetonitrile). The effluent is concentrated under reduced pressure, and the concentrate is lyophilized to give 0.15 g of (S,S,S)-2-[N-[(S)-5-(4-piperidyl)-1-carboxypentyl]-L-alanyl]-2-azabicyclo-[3,3,0]octane-3-carboxylic acid as a colorless powder.

Elemental analysis, for $C_{22}H_{37}N_3O_5 \cdot 3/2H_2O$; Calcd.: C, 58.65; H, 8.95; N, 9.33; Found: C, 58.46; H, 8.80; N, 9.35; SIMS spectrum (m/e): 424(MH+).

EXAMPLE 34

In 100 ml of water is dissolved 20 g of succharose, and 10 g of Baker's yeast (Oriental Dry Yeast) is added to the solution, followed by stirring at 30° C. for 10 minutes. To the mixture is added a solution of 1 g of ethyl 6-(1-benzyloxycarbonyl-4-piperidyl)-2-oxohexanoate in 3 ml of ethanol, and the resulting mixture is stirred for 46 hours. To the mixture is added 150 ml of ethyl acetate and the insoluble material is removed by filtration. The ethyl acetate layer is separated and the aqueous layer is further extracted with ethyl acetate. The ethyl acetate layers obtained are combined, dried (MgSO4) and concentrated under reduced pressure. The residue is purified by silicagel column chromatography to give 0.34 g of ethyl (R)-6-(1-benzyloxycarbonyl-4-piperidyl)-2-hydroxyhexanoate as a colorless oil. The product is converted to its ester of (-)-α-methoxy-α-trifluoromethylphenylacetic acid and subjected to quantitative analysis by high performance liquid chromatography (HPLC). The result is that the enantiomeric excess (% e.e.) is 54%.

EXAMPLE 35 to 37

The α-oxoesters shown in the following Table are reduced by Baker's yeast in the same manner as described in Example 34 to give the corresponding (R)-α-hydroxyesters, respectively.

| Example No. | Starting Material | Product | Yield % (% e.e) |
|---|---|---|---|
| 35 | Z—N⟨piperidyl⟩—(CH$_2$)$_4$—CCOOMe (=O) | Z—N⟨piperidyl⟩—(CH$_2$)$_4$—(R)CHCOOMe (OH) | 52 (37) |
| 36 | Z—N⟨piperidyl⟩—(CH$_2$)$_4$—CCOOPr (=O) | Z—N⟨piperidyl⟩—(CH$_2$)$_4$—(R)CHCOOPr (OH) | 43 (32) |
| 37 | Z—N⟨piperidyl⟩—(CH$_2$)$_4$—CCOOBu (=O) | Z—N⟨piperidyl⟩—(CH$_2$)$_4$—(R)CHCOOBu (OH) | 31 (30) |

Z—: PhCH$_2$OCO—

EXAMPLES 39 to 41

The α-hydroxyesters shown in the following Table are oxidized in the same manner as described in Example 38 to give the corresponding α-oxoesters, respectively.

| Example No. | Starting Material | Product (Yield %) |
|---|---|---|
| 39 | Z—N⟨piperidyl⟩—(CH$_2$)$_4$CHCOOMe (OH) | Z—N⟨piperidyl⟩—(CH$_2$)$_4$CCOOMe (=O) (40%) |
| 40 | Z—N⟨piperidyl⟩—(CH$_2$)$_4$CHCOOPr (OH) | Z—N⟨piperidyl⟩—(CH$_2$)$_4$CCOOPr (=O) (45%) |
| 41 | Z—N⟨piperidyl⟩—(CH$_2$)$_4$CHCOOBu (OH) | Z—N⟨piperidyl⟩—(CH$_2$)$_4$CCOOBu (=O) (75%) |

EXAMPLE 38

To a solution of 2.3 ml of oxalyl chloride in 40 ml of methylene chloride cooled at −65° C. is added a solution of 4.45 g of dimethylsulfoxide in 20 ml of methylene chloride over a period of 10 minutes, and the mixture is stirred at −60° C. for 10 minutes. To the mixture is added a solution of 5 g of ethyl 6-(1-benzyloxycarbonyl-4-piperidyl)-2-hydroxyhexanoate in 50 ml of methylene chloride over a period of 10 minutes, and the resulting mixture is stirred at −60° C. for 20 minutes. To the mixture is added 10.3 g of diethylisopropylamine over a period of 10 minutes, and the temperature is raised from −60° C. up to −30° C. To the mixture is added 80 ml of 1N hydrochloric acid, and the mixture is stirred at room temperature. The methylene chloride layer is separated, washed with water, dried and concentrated under reduced pressure. The residue is purified by silicagel column chromatography (hexane:ethyl acetate=4:1 to 2:1), to give 2.6 g of ethyl 6-(1-benzyloxycarbonyl-4-piperidyl)-2-oxohexanoate as an oil.

EXAMPLE 42

In 0.7 ml of pyridine is dissolved 0.18 g of ethyl (R)-6-(1-benzyloxycarbonyl-4-piperidyl)-2-hydroxyhaxanoate obtained in Example 34, and 0.11 g of methanesulfonyl chloride is added to the mixture under ice-cooling with stirring. After stirring for 2 hours, 0.1 ml of water is added to the mixture and the resulting mixture is stirred for 20 minutes. To the mixture are added 30 ml of water, 5 ml of ethyl acetate and 5 ml of hexane, and the organic layer is separated, washed with water, 1N hydrochloric acid, water, aqueous sodium bicarbonate and water, successively, dried over anhydrous magnesium sulfate and concentrated under reduced pressure to give 0.2 g of ethyl (R)-(1-benzyloxycarbonyl-4-piperidyl)-2-methanesulfonyloxyhexanoate.

EXAMPLE 43

A mixture of 0.32 g of tert-butyl (RS)-3-amino-2-oxo-2,3,4,5-tetrahydro-1H-1-benzazepine-1-acetate and 0.2 g of ethyl (R)-(1-benzyloxycarbonyl-4-piperidyl)-2-methanesulfonyloxyhexanoate is heated at 90° C. for 30 minutes. After cooled, the mixture is separated and purified by silicagel column chromatography (hexane:ethyl acetate=2:1) to give 0.14 g of tert-butyl 3(R)-[5-(1-benzyloxycarbonyl-4-piperidyl)-1(S)-ethoxycarbonylpentyl]amino-2-oxo-2,3,4,5-tetrahydro-1H-1-benzazepine-1-acetate as colorless oil from the first fraction.

IR spectrum $\nu_{max}^{neat}$cm$^{-1}$: 3310(NH); 1730, 1690, 1665 (C=O); Mass spectrum (m/e): 649 (M+).

From the second faraction, 0.12 g of tert-butyl 3(S)-[5-(1-benzyloxycarbonyl-4-piperidyl)-1(S)-ethoxycarbonylpentyl]amino-2-oxo-2,3,4,5-tetrahydro-1H-1-benzazepine-1-acetate is obtained as colorless oil.

IR spectrum $\nu_{max}^{neat}$cm$^{-1}$: 3320(NH); 1730, 1690, 1660 (C=O); Mass spectrum (m/e): 649 (M+).

EXAMPLE 44

3(S)-[5-(1-Benzyloxycarbonyl-4-piperidyl)-1(S)-ethoxycarbonylpentyl]amino-2-oxo-2,3,4,5-tetrahydro-1H-1-benzazepine-1-acetate is treated with hydrogen bromide, subjected to alkaline hydrolysis and purified by XAD-2 column chromatography in the same manner as described in Example 30 to give 0.03 g of 3(S)-[5-(4-piperidyl)-1(S)-carboxypentyl]amino-2-oxo-2,3,4,5-tetrahydro-1H-1-benzazepine-1-acetic acid as a colorless powder.

EXPERIMENTAL EXAMPLE 1

Effect of Compounds of The Present Invention against Hypertensive Activity of Angiotensin I [Experimental Method]

There were used male rats (Sprague-Dawley) weighing 300 to 400 g which were bred under free access to feed and water. The rats were anesthetized by intraperitoneal injection of pentobarbital sodium (50 mg/kg) on the day before the experiment, whereupon polyethylene tubes were inserted into the femoral artery for measurement of blood pressure and the femoral vein for injection of angiotensin I and II, and the tubes were fixed.

On the day of experiment, the average blood pressure in the control phase was measured by use of an electric hemodynamometer (MPU-0.5-290-O-III model, manufactured by NEC-Sanei of Japan) and recorded with a polygraph (365 model manufactured by NEC-Sanei or RM-45 model manufactured by Nippon Kohden of Japan), and thereafter angiotensin I and then angiotensin II were injected through the femoral vein in a dose of 300 ng/kg and 100 ng/kg, respectively, to determine their hypertensive activities. Then, the compound of this invention was administered intravenously as a solution in physiological saline, and angiotensin I and II were injected repeatedly 5, 10, 30, 60, 90 and 120 minutes after the administration, respectively, to trace the hypertensive reactions. In calculating the rate of inhibition against the hypertensive activity of angiotensin I, the rate of inhibition was corrected based on the variation with time in the hypertensive reaction by angiotensin II. [Experimental Results]

The experimental results with compounds of this invention are as shown in Table 6.

TABLE 6

| Test Comp'd. No. of Example | Amount (μg/kg) administered i.v. | Rate (%) of inhibition against hypertensive activity of angiotensin I in relation to time | | | | | |
|---|---|---|---|---|---|---|---|
| | | 5 min. | 10 min. | 30 min. | 60 min. | 90 min. | 120 min. |
| 3 | 300 | 100 | 99 | 100 | 100 | 100 | 98 |
| 6 | 300 | 77 | 84 | 86 | 86 | 80 | 61 |
| 20 | 300 | 100 | 100 | 100 | 100 | 100 | 92 |
| 23 | 600 | 95 | 98 | 100 | 96 | 92 | 94 |
| 31 | 600 | 100 | 100 | 100 | 92 | 83 | 90 |
| 33 | 300 | 100 | 100 | 91 | 91 | 91 | 91 |

What is claimed is:

1. A compound of the formula:

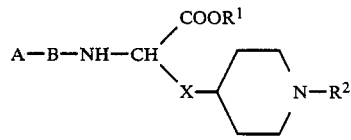

wherein A—B is a group represented by the formula:

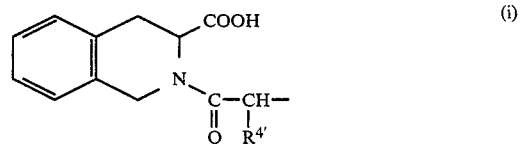

(i)

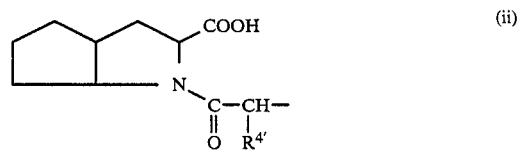

(ii)

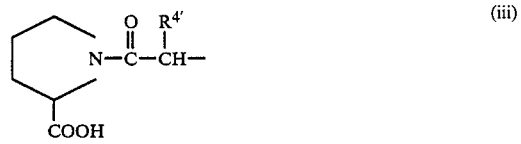

(iii)

or

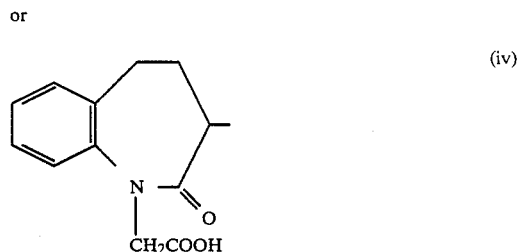

(iv)

wherein R$^4$ is lower alkyl; R$^1$ is hydrogen, lower alkyl or phenyl-lower alkyl; R$^2$ is hydrogen, lower alkyl, phenyl-lower alkyl, lower alkanoyl, benzoyl, phenyl-lower alkoxycarbonyl or lower alkoxycarbonyl; and X is C$_{1-7}$ alkylene; or a pharmaceutically acceptable salt thereof.

2. A compound according to claim 1, wherein A—B is a group represented by the

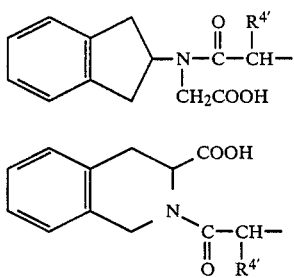

wherein R⁴' is lower alkyl.

3. A compound according to claim 1, which is (S)-2-[N-[N-[(S)-1-carboxy-5-(4-piperidyl)pentyl]-L-alanyl]-1,2,3,4-tetrahydroisoquinoline-3-carboxylic acid.

4. A compound according to claim 1, which is 3(RS)-[5-(4-piperidyl)-1-(RS)-carboxypentyl]amino-2-oxo-2,3,4,5-tetrahydro-1H-benzazepine-1-acetic acid.

5. A compound according to claim 1, which is (S,S,S)-2-[N-[1(S)-5-(4-piperidyl)-1-carboxypentyl]-L-alanyl]-2-azabicyclo[3,3,0octane-3-carboxylic acid.

6. A compound according to claim 1, wherein $R^1$ is hydrogen or lower alkyl.

7. A compound according to claim 1, wherein $R^2$ is hydrogen.

8. A compound according to claim 1, wherein X is trimethylene, tetramethylene or pentamethylene.

9. A compound according to claim 1, wherein X is tetramethylene.

10. A compound according to claim 1, wherein $R^1$ is hydrogen.

* * * * *

UNITED STATES PATENT AND TRADEMARK OFFICE
CERTIFICATE OF CORRECTION

PATENT NO. : 4,871,842

DATED : October 3, 1989

INVENTOR(S) : Hirosada SUGIHARA et al.

It is certified that error appears in the above-identified patent and that said Letters Patent is hereby corrected as shown below:

IN THE CLAIMS:

Claim 1, line 1, after formula (iv), change "$R^4$" to --$R^{4'}$--.

Claim 2, delete the first formula.

Claim 5, line 3, change "[3,3,0octane" to --[3,3,0]octane--.

Signed and Sealed this

Twenty-fifth Day of September, 1990

Attest:

HARRY F. MANBECK, JR.

Attesting Officer  Commissioner of Patents and Trademarks